United States Patent [19]

Earl

[11] Patent Number: 5,580,871

[45] Date of Patent: Dec. 3, 1996

[54] 4-HETEROARYL- 1,4-DIHYDROPYRIDINE COMPOUNDS WITH CALCIUM AGONIST AND ALPHA₁-ANTAGONIST ACTIVITY

[75] Inventor: Richard A. Earl, Wilmington, Del.

[73] Assignee: The Dupont Merck Pharmaceutical Company, Wilmington, Del.

[21] Appl. No.: 401,599

[22] Filed: Mar. 9, 1995

Related U.S. Application Data

[62] Division of Ser. No. 979,679, Nov. 20, 1992, Pat. No. 5,432,188.

[51] Int. Cl.⁶ .................. C07D 405/14; A61K 31/44
[52] U.S. Cl. .................. 514/235.8; 514/241; 514/252; 514/255; 514/256; 514/336; 514/340; 514/341; 514/342; 514/343; 514/338; 544/212; 544/238; 544/333; 544/360; 544/114; 546/114; 546/116; 546/194; 546/257; 546/268.4; 546/268.7; 546/269.1; 546/270.4; 546/272.1; 546/274.1; 546/276.4; 546/276.1; 546/275.4; 546/272.4; 546/280.4; 546/281.4; 546/283.4; 546/284.4; 546/284.7

[58] Field of Search .................. 544/212, 360, 544/333, 238, 114; 514/241, 252, 255, 256, 235.8, 336, 340, 341, 342, 343, 338; 546/255, 271, 276, 279, 280, 281, 283

[56] References Cited

U.S. PATENT DOCUMENTS

| 4,659,717 | 4/1987 | Wikel .................. 514/301 |
| 4,902,694 | 2/1990 | Holland et al. .................. 514/301 |

*Primary Examiner*—Zinna Northington Davis

[57] ABSTRACT

There are provided novel 1,4-dihydropyridine compounds, compositions containing them and methods of using them to treat congestive heart failure.

27 Claims, No Drawings

4-HETEROARYL- 1,4-DIHYDROPYRIDINE COMPOUNDS WITH CALCIUM AGONIST AND ALPHA$_1$-ANTAGONIST ACTIVITY

This is a division of application Ser. No. 07/979,679, filed Nov. 20, 1992, now U.S. Pat. No. 5,432,188.

FIELD OF THE INVENTION

This invention relates to certain novel 1,4-dihydropyridines, processes for their preparation, pharmaceutical compositions containing them, and methods of using them to treat congestive heart failure, and more particularly to such 1,4-dihydropyridines having both calcium agonist and alpha$_1$-antagonist activity and which are useful in the treatment of congestive heart failure.

BACKGROUND OF THE INVENTION

Over the past decade, dihydropyridine calcium antagonists or calcium channel blockers have become widely known therapeutic agents having vasodilator properties which can be used as antihypertensives and coronary dilator agents. These compounds inhibit the entry of calcium ions into cells, or its mobilization from intracellular stores. More recently, it has been found that small structural modifications of these known compounds produce dihydropyridines with effects diametrically opposed to those of calcium channel blockers. Dihydropyridines such as Bay K8644 and CGP 28392 (FIG. 1) promote an influx of calcium ions, into cells thereby producing positive inotropic and vasoconstrictor effects. Bay K8644 is more than ten times as potent as CGP 28392 as a calcium agonist. However, Bay K8644 is not useful as a cardiotonic because of its coronary vasoconstricting properties. Therefore it is only useful as a pharmacological tool to ascertain the function of calcium entry blockers.

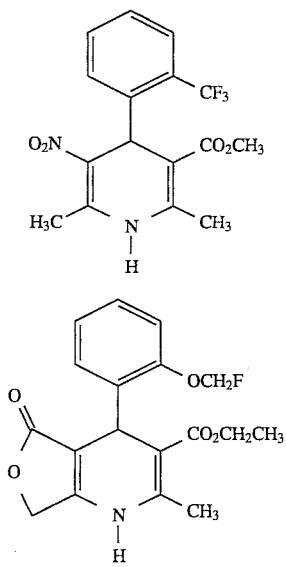

Bay K8644

CGP 28392

Representative of the art in the field of dihydropyridine calcium agonists are U.S. Pat. No. 4,248,873 (Bossert et al.) issued Feb. 3, 1981, European Patent Application 0071819 published Feb. 16, 1983 (Boshagen et al.), U.S. Pat. No. 4,537,881 (Franckowiah et al.) issued Aug. 27, 1985 and U.S. Pat. No. 4,532,248 issued Jul. 30, 1985 which describes dihydropyridine calcium agonists which contain an amino group in the 2-position. Literature references include M. Schram, et al., *Nature*, 303, 535 (1983); M. Schram, et al., *Arzneim-Forsch.*, 33, 1268 (1983); P. Erne, et al., *Biochem. Biophys. Res. Commun.*, 118, 842 (1984).

Combining calcium agonist properties and alpha$_1$-adrenergic blocking properties in a single molecular structure provides a new and attractive principle for the treatment of congestive heart failure. The combination of these two types of activities affords a novel class of cardiotonics which have cardiac stimulatory effects in combination with pronounced vasodilator properties. The detrimental vasoconstricting properties which are normally associated with dihydropyridine calcium agonists are minimized by the alpha$_1$-adrenergic blocking properties which cause dilation of the peripheral vasculature. Applicants are not aware of any references that describe the combination of these actions in a single compound, other than co-assigned U.S. Pat. No. 4,868,181 (Johnson et al.) issued Sep. 19, 1989.

SUMMARY OF THE INVENTION

According to the present invention there is provided novel 1,4-dihydropyridine derivatives of the general formula (I) which possess both calcium channel promoting activity and alpha$_1$-adrenergic blocking properties and are useful in the treatment of congestive heart failure. These compounds have the formula:

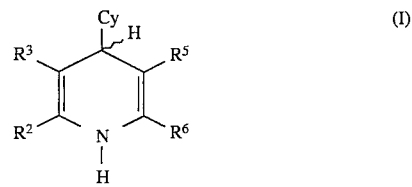

or a pharmaceutically acceptable salt thereof or an optically active isomer or N-oxide thereof wherein:

$R^2$ and $R^6$ independently are alkyl of 1–4 carbon atoms, CN, CH$_2$OH or CH$_2$OCH$_2$CH$_2$NH$_2$;

$R^3$ independently is NO$_2$, H, CN, CONH$_2$, or taken together with $R^2$ is

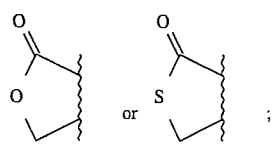

Cy, when $R^5$ is CHO, COCH$_3$, CO$_2$CH$_2$CHOHC$_6$H$_5$, CO$_2$CH(OCH$_3$)C$_6$H$_5$, NO$_2$, CONHC$_6$H$_5$ or an alkyl ester of 1–10 carbon atoms, is:

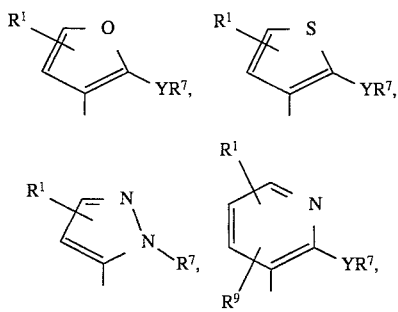

-continued

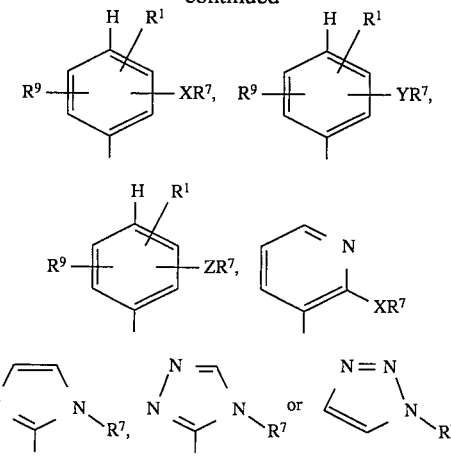

R¹ and R⁹ independently are H, alkyl of 1–4 carbon atoms, haloalkyl of 1–4 carbon atoms, alkoxy of 1–10 carbon atoms, halogen or NO₂;

Cy, when R⁵ is COR⁷, CO₂R⁷ or CONHR⁷, is: 3-, or 4-pyridinyl; 2- or 3-furanyl; 2- or 3-thienyl, 4-, or 5-thiazolyl, 2-, 4-, or 5-pyrimidinyl or

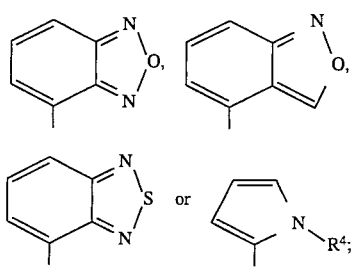

X is SO, SO₂, NR⁴, O, S or N→O;
Y is

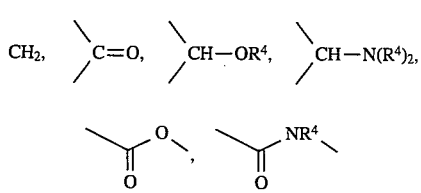

Z is

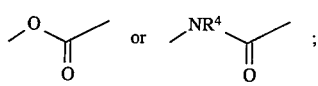

R⁴ is H or an alkyl group of 1–4 carbon atoms;
R⁷ is

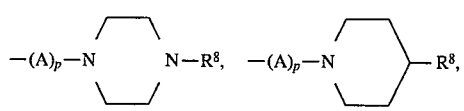

-continued

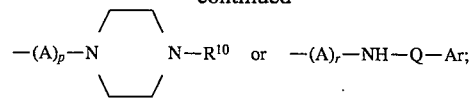

A is a straight or branched alkyl, alkenyl, or alkynyl chain or —(CH₂)$_n$CHOHCH₂—;
R¹⁰ is

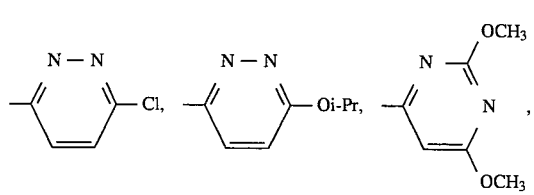

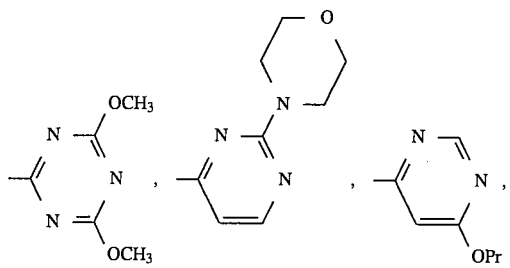

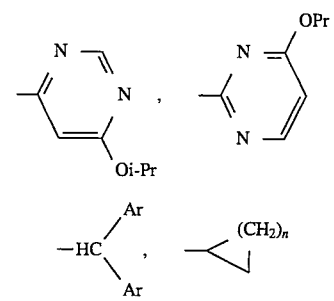

or 2-, 3-, or 4-pyridinyl; 2-, or 4-pyrimidinyl; or 2-pyrazinyl;
R⁸ is

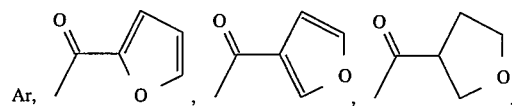

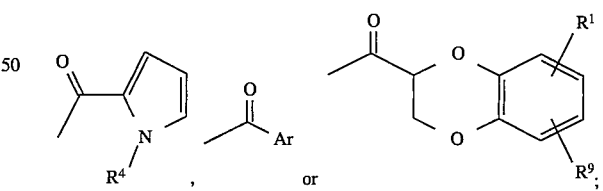

Ar is phenyl optionally substituted with one or two substituents independently selected from the group consisting of:
alkyl of 1–4 carbon atoms, haloalkyl of 1–4 carbon atoms, alkoxy of 1–4 carbon atoms, halogen, or NO₂, provided that Ar is not 4-fluorophenyl;
Q is (CH₂)$_q$, (CH₂)$_n$O, (CH₂)$_n$NH or (CH₂)$_n$S;
n is independently 1–4;

p is 1 to 10;
q is 0–2; and
r is 1 to 10, with the following proviso: when Cy is

[structure: phenyl ring with H, R¹, R⁹, XR⁷ substituents]

and X is O, S or NH, then, $R^7$ cannot be —$(A)_r$—NH—Q—Ar, where A is as defined above;

$R^8$ cannot be Ar; and $R^{10}$ cannot be 2-, 3-, or 4-pyridinyl or 2-, or 4-pyrimidinyl.

The compounds of the present invention can exist as optical isomers and both the racemates as well as the individual optical isomer which confers agonist activity are within the scope of the present invention. The racemic mixtures can be separated into their individual isomers by well known techniques such as the separation of the diastereomeric salts formed with optically active acids, followed by conversion back to the optically active 1,4-dihydropyridine.

Also provided are pharmaceutical compositions comprising a suitable pharmaceutical carrier and a compound of formula (I) and methods of using the compounds of formula (I) to treat congestive heart failure.

Further provided are processes for preparing compounds of formula (I), which processes will be described in detail hereinafter.

PREFERRED EMBODIMENTS

Preferred compounds are those of formula (I) wherein:

(A) (1) $R^2$ is $CH_3$; and/or (2) $R^3$ is $NO_2$; and/or (3) Cy is

[structure: 5-membered ring with R¹, O, YR⁷]

and/or (4) $R^5$ is an alkyl ester of 1–4 carbon atoms, wherein: (a) $R^1$ is H; and/or (b) Y is $CH_2$ and/or (c) $R^7$ is —$(A)_p$—N⟨ ⟩N—$R^8$   or   —$(A)_p$—N⟨ ⟩N—$R^{10}$;

wherein (i) A is —$(CH_2)_p$— where p is 1 to 5; and/or
(ii) $R^8$ is Ar where Ar is phenyl optionally monosubstituted with $OCH_3$, $CH_3$, or Cl; or $R^8$ is

[structure: furan-2-yl acetyl]

and/or (iii) $R^{10}$ is 2- or 4-pyrimidinyl.

(B) (1) $R^2$ is $CH_3$; and/or (2) $R^3$ is $NO_2$; and/or (3) Cy is

[structure: phenyl with H, R¹, R⁹, XR⁷]

and/or (4) $R^5$ is an alkyl ester of 1–4 carbon atoms, wherein; (a) $R^1$ is H; and/or (b) X is O; and/or (c) $R^7$ is —$(A)_p$—N⟨ ⟩N—$R^8$   or   —$(A)_p$—N⟨ ⟩—Ph;

wherein:

(i) A is —$(CH_2)_p$— (p=1–5); and/or
(ii) $R^8$ is selected from the group consisting of:

[structures: furan-2-yl acetyl; pyridazinyl-Cl; pyridazinyl-Oi-Pr]

(C) (1) $R^2$ is $CH_3$; and/or (2) $R^3$ is $NO_2$; and/or (3) Cy is

[structure: phenyl with H, R¹, R⁹, XR⁷]

and/or (4) $R^5$ is an alkyl ester of 1–4 carbon atoms, wherein; (a) $R^1$ is H; and/or (b) X is $SO_2$; and/or (c) $R^7$ is —$(A)_p$—N⟨ ⟩N—$R^8$   or   —$(A)_p$—N⟨ ⟩—Ph;

wherein:

(i) A is —$(CH_2)_p$— (p=1–5); and/or
(ii) $R^8$ is Ar, where Ar is phenyl optionally monosubstituted with $OCH_3$, $CH_3$ or Cl, or is selected from the group consisting of:

[structures: furan-2-yl acetyl; pyridazinyl-Cl; pyridazinyl-Oi-Pr]

(D) (1) $R^2$ is $CH_3$; and/or (2) $R^3$ is $NO_2$; and/or (3) Cy is 2- or 3-furanyl; 2- or 3-thienyl; 3-pyridinyl;

[structures: benzofurazan or pyrrole-N-$R^4$]

and/or (4) $R^5$ is $CO_2R^7$; where; (a) $R^7$ is

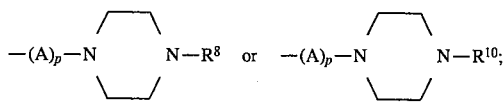

wherein:
(i) A is $-(CH_2)_p-$ (p=1–5); and/or
(ii) $R^8$ is Ar where Ar is phenyl optionally monosubstituted with $OCH_3$, $CH_3$, or Cl; and/or
(iii) $R^{10}$ is 2- or 4-pyrimidinyl.

SPECIFICALLY PREFERRED COMPOUNDS (1) 1,4-Dihydro-4-(2-{5-[4-(2-methoxyphenyl)-1-piperazinyl]pentyl}-3-furanyl)-2,6-dimethyl-5-nitro-3-pyridinecarboxylic acid, methyl ester
(2) 4-(4-Benzofurazanyl)-1,4-dihydro-2,6-dimethyl-5-nitro-3-pyridinecarboxylic acid, {4-[4-(2-methoxyphenyl)-1-piperazinyl]butyl} ester
(3) 1,4-Dihydro-2,6-dimethyl-5-nitro-4-(3-pyridinyl)-3-pyridinecarboxylic acid, {4-[4-(2-pyrimidinyl)-1-piperazinyl]butyl} ester
(4) 4-(3-Furanyl)-1,4-dihydro-2,6-dimethyl-5-nitro-3-pyridinecarboxylic acid, {2-[4-(2-methoxyphenyl)-1-piperazinyl]ethyl} ester
(5) 4-(3-Furanyl)-1,4-dihydro-2,6-dimethyl-5-nitro-3-pyridinecarboxylic acid, {2-[4-(2-pyrimidinyl)-1-piperazinyl]ethyl} ester
(6) 1,4-Dihydro-2,6-dimethyl-4-(1-methyl-1H-pyrrol-2-yl)-5-nitro-3-pyridinecarboxylic acid, {4-[4-(2-methoxyphenyl)1-piperazinyl]butyl} ester
(7) 1,4-Dihydro-2,6-dimethyl-4-(1-methyl-1H-pyrrol-2-yl)-5-nitro-3-pyridinecarboxylic acid, {4-[4-(2-pyrimidinyl)-1-piperazinyl]butyl} ester
(8) 1,4-Dihydro-2,6-dimethyl-5-nitro-4-(3-thienyl)-3-pyridinecarboxylic acid, {2-[4-(2-methoxyphenyl)-1-piperazinyl]ethyl} ester
(9) 1,4-Dihydro-2,6-dimethyl-5-nitro-4-(3-thienyl)-3-pyridinecarboxylic acid, {2-[4-(2-pyrimidinyl)-1-piperazinyl]ethyl} ester
(10) 4-(3-Furanyl)-1,4-dihydro-2,6-dimethyl-5-nitro-3-pyridinecarboxylic acid, {4-[4-(2-pyrimidinyl)-1-piperazinyl]butyl} ester
(11) 4-(2-Furanyl)-1,4-dihydro-2,6-dimethyl-5-nitro-3-pyridinecarboxylic acid, {4-[4-(2-pyrimidinyl)-1-piperazinyl]butyl} ester
(12) 1,4-Dihydro-2,6-dimethyl-5-nitro-4-(2-thienyl)-3-pyridinecarboxylic acid, {2-[4-(2-methoxyphenyl)-1-piperazinyl]ethyl} ester
(13) 1,4-Dihydro-2,6-dimethyl-4-(1-methyl-1H-pyrrol-2-yl)-5-nitro-3-pyridinecarboxylic acid, {2-[4-(2-methoxyphenyl)-1-piperazinyl]ethyl} ester
(14) 1,4-Dihydro-2,6-dimethyl-4-(1-methyl-1H-pyrrol-2-yl)-5-nitro-3-pyridinecarboxylic acid, {2-[4-(2-pyrimidinyl)-1-piperazinyl]ethyl} ester

DETAILED DESCRIPTION OF THE INVENTION

Synthesis

The dihydropyridines of the general formula (I), can be prepared by the processes illustrated below. It is understood in all of these processes that $R^1-R^{10}$, Ar, X, Y, A, p, r, Q, n, q are as defined above. Methods A–F are substantially the same as described in commonly assigned U.S. Pat. No. 4,868,181 which is herein incorporated by reference.

Compounds of the formula CyCHO (2) are commercially available, or may be prepared by methods described in the literature. The heterocyclic aldehydes used as intermediates are available by methods described in standard works on heterocyclic chemistry such as Katritzsky and Rees, *Comprehensive Heterocyclic Chemistry*, vols. 2–5, Pergamon Press, N.Y., 1984. In some instances, the preparation of the hydroxymethyl compounds are described in the literature. These can be converted to the corresponding aldehydes by known methods, such as oxidation with manganese dioxide, or dimethysulfoxide activated with oxalyl chloride.

Compounds of the formula 6 may be prepared according to Method 1, where X" is $NR^4$, O, or S, and $R^{12}$ is $CO_2R^4$ or $CH_2OH$ (or a protected alcohol). Compound 3 is alkylated with an appropriate connector chain 4 to give compound 5. This reaction is carried out in the presence of an aromatic hydrocarbon such as benzene, toluene, etc., a halogenated hydrocarbon such as dichloromethane, carbon tetrachloride, etc., an ether such as THF, DME, etc., or an aprotic solvent such as acetonitrile, DMF, etc., in the presence of a base such as potassium carbonate, sodium carbonate, sodium bicarbonate, or sodium hydride, at a temperature in the range of −20° C. to 200° C., preferably of 25° C. to 150° C. Separation of the desired product from the reaction mixture is effected by conventional operations such as filtration, concentration, extraction, column chromatography, recrystallization, etc.

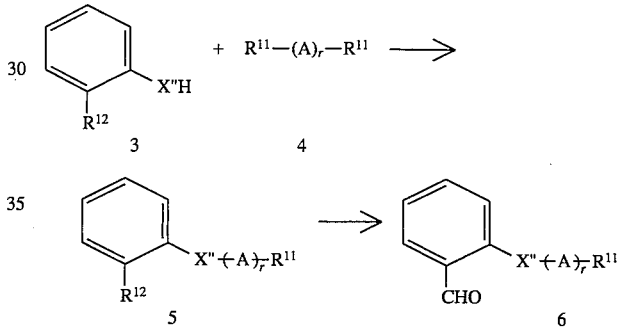

Compounds of the formulas 7, 8, 9, and 10 may be purchased commercially, or prepared according to the methods described by S. F. Campbell, et al., *J. Med. Chem.*, 30, 49, 999, 1794 (1987), and by other methods reported in the literature.

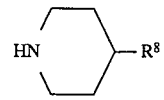

7

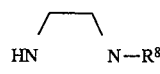

8

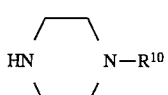

9

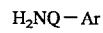

10

Compounds of the formula 13 may be prepared according to Method 2. Compound 11 (prepared according to Methods A–D) is converted to the carboxylic acid with a fluoride source, such as tetrabutylammonium fluoride or hydrogen fluoride. Treatment with 1,1'-carbonyldiimidazole provides the activated imidazolide 12, which may be reacted with alcohols of the type $R^7OH$ to produce 13.

Method 2

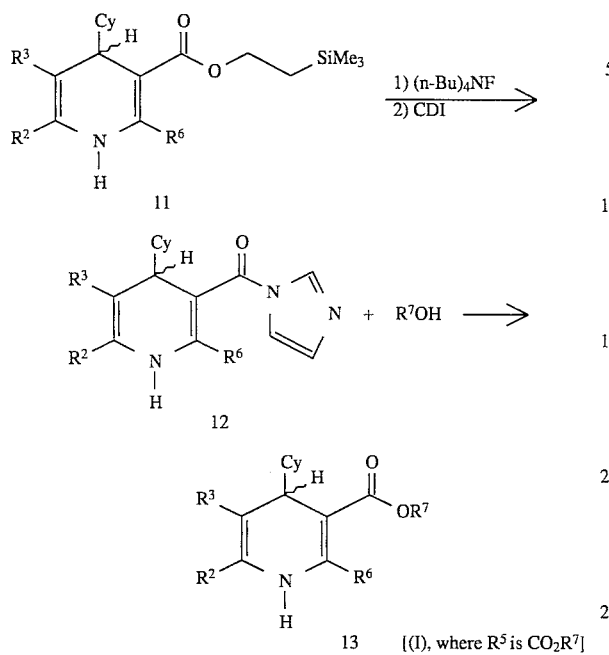

As shown in Method 3, compounds of the formulas 15 and 17 may be prepared by reacting compounds of the formulas 14 and 16 with amines 7 or 8 or 9 or 10, respectively. The reaction is carried out by reacting 14 or 16 with amines 7 or 8 or 9 or 10 in a molar ratio of 1.0:1.0 to 1.0:4.0 in the presence of a base such as potassium carbonate, sodium carbonate, sodium bicarbonate, triethylamine, or sodium hydroxide. The reaction is performed in the presence of an alcoholic solvent such as methanol, ethanol, i-propanol or n-butanol, an aromatic hydrocarbon such as benzene or toluene, an ether such as tetrahydrofuran (THF) or dioxane, a halogenated hydrocarbon such as chloroform or carbon tetrachloride, an aprotic polar solvent such as acetonitrile, dimethylformamide (DMF) or dimethylsulfoxide (DMSO), or the like at a temperature in the range of room temperature to 200° C., preferably at about 25° C.–110° C. Separation of the desired product from the reaction mixture is effected by conventional techniques such as filtration, concentration, extraction, column chromatography, recrystallization, etc.

This method is also applicable for compounds of the Formula 16, where Y or Z is substituted for X.

Method 3

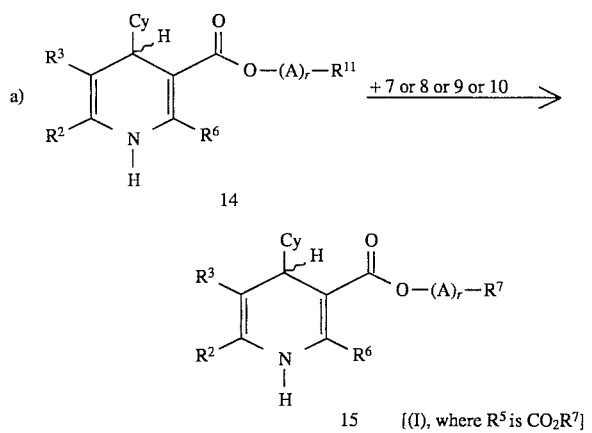

Method 3
-continued

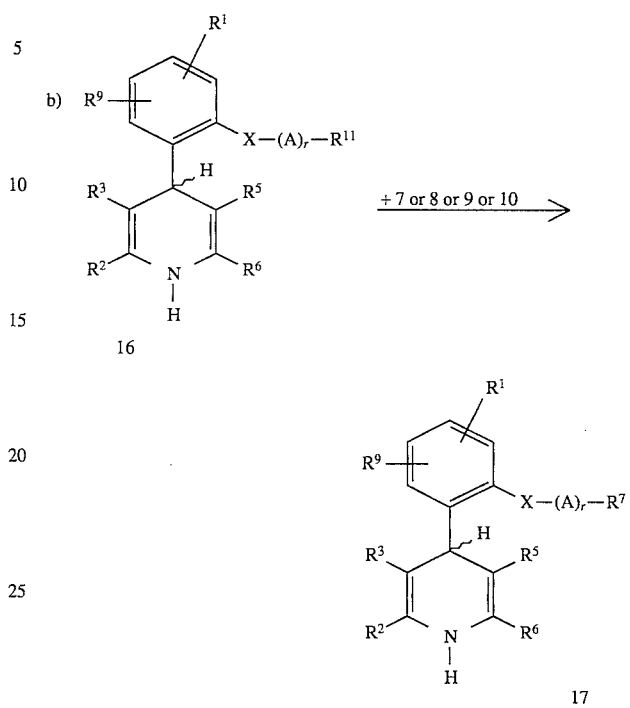

Where X is $NR^4$ or S, 17 can be oxidized to $R^4N \rightarrow O$ or SO or $SO_2$, respectively, with an oxidizing agent such as hydrogen peroxide, peracetic acid, m-chloroperbenzoic acid, etc.

Compounds of the formula 19, where $R^{13}$ is S or O, (Method 4) may be prepared according to procedures described in the literature, such as I. Sircar, et al., Tetrahedron Lett. 29, 6835 (1988) and U.S. Pat. No. 4,642,310, issued Feb. 10, 1987.

Method 4

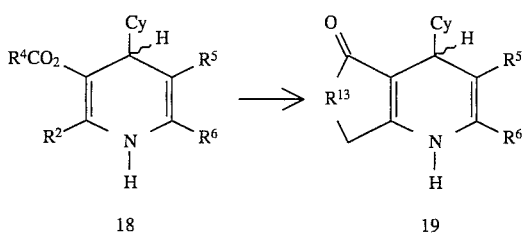

The above preparation processes are given merely for illustration. The preparation of the compounds of the formula (I) is not limited to these processes, but any modification of these processes can be applied in the same manner to the preparation of the compounds according to the invention.

A resulting basic compound can be converted into a corresponding acid addition salt by reacting it with an inorganic or organic acid as is well known to one skilled in the art. Therapeutically useful acids include, for example, inorganic acids, such as hydrochloric, hydrobromic, sulfuric, phosphoric or nitric, or organic acids, such as formic, acetic, propionic, succinic, maleic, fumaric, tartaric or ascorbic acid.

The compounds of this invention and their preparation can be understood further by the following examples, but should not constitute a limitation thereof. In these examples, unless otherwise indicated, all temperatures are in degrees Celsius and parts and percentages are by weight.

EXAMPLE 1

Part A; 2-(5-Chloropentyl)-3-furanmethanol: To a solution of 3-furanmethanol (3.56 g) in THF (200 ml) at −20° C., was added n-butyllithium (50 ml of 1.6M in hexane). The solution was kept at 0° C. for 4 hrs., then 5-chloro-1-iodopentane (8.37 g) was added. The mixture was stirred at room temperature for 4 days, after which water (500 ml) and ether (500 ml) were added. The organic layer was separated and dried over magnesium sulfate and the solvent was removed by rotary evaporation to give an oil. Purification by column chromatography on silica gel, using hexane:ethyl acetate (1:1) as the eluent provided the pure product, 5.6 g. $^1$H-NMR (CDCl$_3$) δ 1.50 (m, 2H); 1.67 (m, 2H); 1.80 (m, 2H); 2.64 (t, 2H, J=7 Hz); 3.52 (t, 2H, J=7 Hz); 4.46 (s, 2H); 6.04 (s, 1H); 6.36 (s, 1H).

Part B; 2-(5-Chloropentyl)-3-furanaldehyde: To a 500 ml 4-neck round-bottom flask fitted with mechanical stirrer, thermowell, and addition funnel, under a nitrogen atmosphere, was added 7.4 ml of oxalyl chloride and 150 ml of dichloromethane. The reaction was cooled to −78° C. with a dry ice/acetone bath. Then 12.58 ml of distilled dimethylsulfoxide in 38 ml of dichloromethane was added dropwise, maintaining the reaction temperature below −65° C. After the addition was complete, 15 g of 2-(5-chloropentyl)-3-furanmethanol was added in 74 ml of dichloromethane. After addition was complete, the mixture was stirred for 30 min., then 52 ml of triethylamine was added. The bath was allowed to warm gradually to room temperature, and stirred overnight at this temperature. The reaction mixture was poured into a 1 liter flask containing a stirring mixture of 310 g of crushed ice and 47 ml of 1N HCl. After stirring for 30 min., the mixture was extracted with dichloromethane (3×100 ml). The organic solution was dried over magnesium sulfate, filtered and concentrated to a brown oil. The product was further purified by column chromatography on silica gel, eluting with 10% ethyl acetate in hexane to give 12.75 g of the purified product as an oil. $^1$H-NMR (CDCl$_3$) δ 1.52 (m, 2H); 1.79 (m, 4H); 2.98 (t, 2H, J=7 Hz); 3.54 (t, 2H, J=7 Hz); 6.70 (d, 1H, J=2 Hz); 7.33 (d, 1H, J=2 Hz); 9.95 (s, 1H).

Part C; 1,4-Dihydro-4-[2-(5-chloropentyl)-3-furanyl]-2,6-dimethyl-5-nitro-3-pyridinecarboxylic acid, methyl ester: A mixture of 2-(5-chloropentyl)-3-furanaldehyde (10.2 g), nitroacetone (7.9 g), and methyl 3-aminocrotonate (5.9 g) in 250 ml of ethanol was heated at reflux for 18 hrs. After removal of the solvent by rotary evaporation, the residue was purified via column chromatography on silica gel, eluting with 30% petroleum ether in diethyl ether, to give a yellow solid. Recrystallization from chloroform/diethyl ether produced yellow crystals, 3.2 g, m.p. 133°–135° C. $^1$H-NMR (CDCl$_3$) δ 1.65 (m, 4H); 1.87 (m, 2H); 2.36 (s, 3H); 2.52 (s, 3H); 2.78 (m, 2H); 3.56 (t, 2H, J=7 Hz); 3.69 (s, 3H); 5.29 (s, 1H); 5.98 (d, 1H, J=1 Hz); 6.07 (d, 1H, J=1 Hz); 7.14 (d, 1H, J=1 Hz). Mass spectrum: 383 (M+H). IR (KBr): 3311, 2952, 1706, 1654, 1491, 1450, 1220 cm$^{-1}$.

Part D; 1,4-Dihydro-4-(2-{5-[4-(2-methoxyphenyl)-1-piperazinyl]pentyl}-3-furanyl)-2,6-dimethyl-5-nitro-3-pyridinecarboxylic acid, methyl ester: A mixture of 1,4-dihydro-4-[2-(5-chloropentyl)-3-furanyl]-2,6-dimethyl-5-nitro-3-pyridinecarboxylic acid, methyl ester (1.0 g), 0.9 g of 1-(2-methoxyphenyl)piperazine, 75 mg of sodium iodide, and 0.4 g of sodium bicarbonate in 100 ml of acetonitrile was heated at reflux for 6.5 hrs., then stirred overnight at room temperature. The solvent was removed by rotary evaporation, and the residue was partitioned between dichloromethane and water. The aqueous layer was washed with dichloromethane (2×100 ml), the organic layers combined, washed with water, dried over magnesium sulfate, filtered, and concentrated. The crude product was purified by column chromatography, eluting with 5% methanol in dichloromethane. The product (Ex. No. 1, Table 1) was isolated as an orange solid, 1.07 g., m.p. 94°–105° C. $^1$H-NMR (CDCl$_3$) δ 1.45 (m, 2H); 1.69 (m, 6H); 2.37 (s, 3H); 2.51 (m, 1H); 2.77 (m, 5H); 3.28 (m, 4H); 3.68 (s, 3H); 3.87 (s, 3H); 5.30 (s, 1H); 6.11 (d, 1H, J=2 Hz); 6.30 (br. s., 1H); 6.95 (m, 4H); 7.14 (d, 1H, J=2 Hz). IR (KBr):2942, 1709, 1651, 1501, 1317, 1225 cm$^{-1}$. Mass Spectrum: 539 (M+1), 211 (DHP nucleus). HRMS: Calcd: 538.2791; Found: 538.2795

EXAMPLE 53

Part A; 1,4-Dihydro-2,6-dimethyl-5-nitro-4-(3-pyridinyl)-3-pyridinecarboxylic acid, (4-chlorobutyl) ester: A mixture of nitroacetone (3.41 g), 3-pyridinecarboxaldehyde (2.36 g), and (4-chlorobutyl)-3-aminocrotonate (4.22 g) in 100 ml ethanol was heated to reflux for 4 hrs., then stirred at room temperature for 16 hrs. After removal of the solvent by rotary evaporation, the residue was purified via column chromatography on silica gel, eluting with 15% methanol in ethyl acetate, to give a yellow solid, 4.13 g, m.p. 153°–156° C. (dec). $^1$H-NMR (CDCl$_3$) δ 1.72 (m, 4H); 2.37 (s, 3H); 2.52 (s, 3H); 3.50 (t, 2H, J=6 Hz); 4.10 (t, 2H, J=6 Hz); 5.38 (s, 1H); 7.26 (dd, 1H, J=8, 5 Hz); 7.77 (dd, 1H, J=2, 8 Hz); 8.01 (s, 1H); 8.43 (dd, 1H, J=2, 5 Hz); 8.50 (d, 1H, J=2 Hz). Mass spectrum: 366 (M+H).

Part B; 1,4-Dihydro-2,6-dimethyl-5-nitro-4-(3-pyridinyl)-3-pyridinecarboxylic acid: {4-[4-(2-pyrimidinyl)-1-piperazinyl]butyl} ester: To a 100 ml 3-neck round-bottom flask fitted with mechanical stirrer, reflux condenser, and thermowell, under a nitrogen atmosphere, was added 1.0 g of 1,4-dihydro-2,6-dimethyl-5-nitro-4-(3-pyridinyl)-3-pyridinecarboxylic acid, (4-chlorobutyl) ester, 80 ml of DME, 1.79 g of 1-(2-pyrimidinyl)piperazine, 0.10 g of sodium iodide, and 0.5 g of sodium bicarbonate. The reaction mixture was heated at reflux overnight. The solvent was removed by rotary evaporation, and the residue was partitioned between dichloromethane and water. The aqueous layer was washed with dichloromethane (2×200 ml), the organic layers combined, washed with water, dried over magnesium sulfate, filtered, and concentrated. The crude product was purified by column chromatography, eluting with 10% methanol in ethyl acetate. The product (Ex. No. 53, Table 2) was isolated as an orange solid, 0.79 g, m.p. 155°–160° C. (dec). $^1$H-NMR (CDCl$_3$) δ 1.40–1.66 (m, 4H); 2.33 (m, 2H); 2.40 (s, 3H); 2.46 (m, 4H); 2.53 (s, 3H); 3.79 (m, 4H); 4.10 (t, 2H, J=6 Hz); 5.40 (s, 1H); 6.48 (t, 1H, J=6 Hz); 6.96 (s, 1H); 7.23 (m, 1H); 7.73 (m, 1H); 8.31 (d, 2H, J=6 Hz); 8.43 (m, 1H); 8.54 (d, 1H, J=1 Hz). IR (KBr): 3189, 2944, 1706, 1650, 1587, 1548, 1500, 1360, 1225 cm$^{-1}$. Mass Spectrum: 494 (M+1), 522 (M+29), 219 (C$_{12}$H$_{19}$N$_4$).

EXAMPLE 77

Part A; 1,4-Dihydro-2,6-dimethyl-4-(1-methyl-1H-pyrrol-2-yl)-5-nitro-3-pyridinecarboxylic acid, (2-chloroethyl) ester: A mixture of nitroacetone (6.82 g), 1-methyl-2-pyrrolecarboxaldehyde (4.80 g), (2-chloroethyl)-3-aminocrotonate (7.20 g) and 10 g molecular sieves in 200 ml ethanol was stirred at room temperature for 4 days. After removal of the solvent by rotary evaporation, the residue was purified via column chromatography on silica gel, eluting with 30% petroleum ether in diethyl ether, to give a brown solid, 2.36 g. $^1$H-NMR (CDCl$_3$) δ 2.49 (s, 3H); 2.52 (s, 3H); 3.66 (t, 2H, J=6 Hz); 3.87 (s, 3H); 4.35 (t, 2H, J=6 Hz); 5.29 (s, 1H); 5.89 (m, 1H); 5.97 (m, 1H); 6.16 (br. s, 1H); 6.43 (m, 1H).

Part B; 1,4-Dihydro-2,6-dimethyl-4-(1-methyl-1H-pyrrol-2-yl)-5-nitro-3-pyridinecarboxylic acid, {2-[4-(2-methoxyphenyl)-1-piperazinyl]ethyl} ester: A mixture of 1,4-dihydro-2,6-dimethyl-4-(1-methyl-1H-pyrrol-2-yl)-5-nitro-3-pyridinecarboxylic acid, (2-chloroethyl) ester 1.36 g, 1.54 g of 1-(2-methoxyphenyl)piperazine, 133 mg of sodium iodide, and 0.7 g of sodium bicarbonate in 100 ml of DME was heated at reflux for 4 days. The solvent was removed by rotary evaporation, and the residue was partitioned between dichloromethane and water. The aqueous layer was washed with dichloromethane (2×100 ml), the organic layers combined, washed with water, dried over magnesium sulfate, filtered, and concentrated. The crude product was purified by column chromatography, eluting with ethyl acetate. The product (Ex. No. 77, Table 2) was isolated as an orange solid, 0.71 g. $^1$H-NMR (CDCl$_3$) δ 2.38 (s, 3H); 2.51 (s, 3H); 2.65 (m, 6H); 3.05 (s, 4H); 3.86 (s, 6H); 4.25 (t, 2H, J=6 Hz); 5.30 (s, 1H); 5.87 (t, 1H, J=2 Hz); 5.88 (s, 1H); 5.96 (t, 1H, J=3 Hz); 6.43 (t, 1H, J=3 Hz); 6.92 (m, 4H). IR (KBr): 3318, 3096, 2941, 2819, 1687, 1500, 1312, 1102, 1014, 750 cm$^{-1}$. Mass Spectrum: 496 (M+1), 524 (M+29).

Other compounds which can be prepared by such procedures and procedures described in the synthesis disclosure are illustrated by the structures represented in Tables 1 and 2. These Tables are intended to illustrate the invention, but not limit its breadth.

TABLE 1
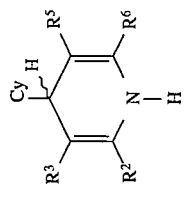
(I)
| Ex. No. | Cy | R² | R³ | R⁵ | R⁶ | mp °C. |
|---|---|---|---|---|---|---|
| 1 | 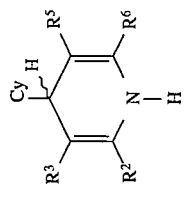 | CH₃ | NO₂ | CO₂CH₃ | CH₃ | 94–105[a] |
| 2 | 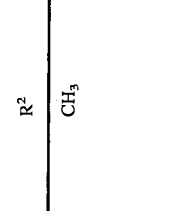 | CH₃ | NO₂ | CO₂CH₃ | CH₃ | 105–8[b] |
| 3 | 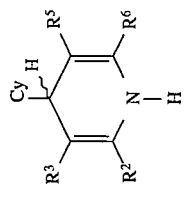 | CH₃ | NO₂ | CO₂CH₃ | CH₃ | 123[c] |
| 4 | 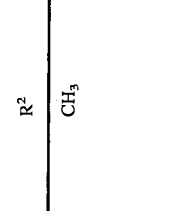 | CH₃ | NO₂ | CO₂CH₃ | CH₃ | 206[d] |
| 5 | 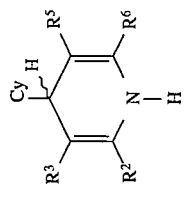 | CH₃ | NO₂ | CO₂CH₃ | CH₃ | 97–111[e] |

TABLE 1-continued (I)

[structure: dihydropyridine with R2, R3, R5, R6 substituents, Cy-H group, NH]

| Ex. No. | Cy | R² | R³ | R⁵ | R⁶ | mp °C. |
|---|---|---|---|---|---|---|
| 6 | 2-(5-(4-phenylpiperidin-1-yl)pentyloxy)phenyl | CH₃ | NO₂ | CO₂CH₃ | CH₃ | 182-6[f] |
| 7 | 2-(5-(4-(6-chloropyridazin-3-yl)piperazin-1-yl)pentyloxy)phenyl | CH₃ | NO₂ | CO₂CH₃ | CH₃ | 164-6[g] |
| 8 | 2-(5-(4-(6-isopropoxypyridazin-3-yl)piperazin-1-yl)pentyloxy)phenyl | CH₃ | NO₂ | CO₂CH₃ | CH₃ | 97-105[h] |
| 9 | 2-(5-(4-(1,4-benzodioxan-2-ylcarbonyl)piperazin-1-yl)pentyloxy)phenyl | CH₃ | NO₂ | CO₂CH₃ | CH₃ | 80-84[i] |
| 10 | 2-(5-(4-(pyrazin-2-yl)piperazin-1-yl)pentyloxy)phenyl | CH₃ | NO₂ | CO₂CH₃ | CH₃ | 66-69[j] |

TABLE 1-continued (I)

| Ex. No. | Cy | R² | R³ | R⁵ | R⁶ | mp °C. |
|---|---|---|---|---|---|---|
| 11 | 2-[O(CH₂)₅-N(piperazine)-C(=CH-C(OPr)=N-CH=N)]phenyl | CH₃ | NO₂ | CO₂CH₃ | CH₃ | glassy solid[k] |
| 12 | 2-[O(CH₂)₃-N(piperazine)-(5-OiPr-pyridin-2-yl via N=N)]phenyl | CH₃ | NO₂ | CO₂CH₃ | CH₃ | |
| 13 | 2-[S(CH₂)₃-N(piperazine)-(4,6-di-OCH₃-pyrimidin-2-yl)]phenyl | CH₃ | NO₂ | CO₂C₂H₅ | CH₃ | |
| 14 | 2-[SO(CH₂)₃-N(piperazine)-(4,6-di-OCH₃-pyrimidin-2-yl)]phenyl | CH₃ | γ-butyrolactone (3-yl) | CO₂CH₃ | CH₃ | |
| 15 | 5-[(CH₂)₃-N(piperazine)-(pyrimidin-2-yl)]pyrazol-3-yl | C₂H₅ | NO₂ | CO₂CH₃ | C₂H₅ | |

TABLE 1-continued (structure shown: dihydropyridine with Cy-CH substituent, R5, R6, R3, R2, N-H)

| Ex. No. | Cy | R² | R³ | R⁵ | R⁶ | mp °C. |
|---|---|---|---|---|---|---|
| 16 | 4-(4-chlorobenzoyl)piperidin-1-yl-propyl-thiophene | CH₃ | CN | CO₂CH₃ | CH₂OH | |
| 17 | benzodioxine-carbonyl-piperazinyl-butyl-imidazole | CH₃ | H | CO₂C₃H₇ | CH₃ | |
| 18 | 4-(2-methoxyphenyl)piperazin-1-yl-propyl-oxy-pyridine | CH₃ | CONH₂ | CO₂CH₃ | CH₃ | |
| 19 | 4-(2-chlorophenyl)piperazin-1-yl-butyl-thio-pyridine | CH₃ | NO₂ | CO₂C₂H₅ | CH₃ | |
| 20 | 4-(pyrimidin-2-yl)piperazin-1-yl-propyl-oxycarbonyl-pyridine | C₃H₇ | H | CO₂CH₃ | CH₃ | |

TABLE 1-continued

| Ex. No. | Cy | R² | R³ | R⁵ | R⁶ | mp °C. |
|---|---|---|---|---|---|---|
| 21 | furan-2-yl carbonyl piperazine linked via butyl ester to furan-2-yl | CH₃ | NO₂ | CO₂CH₃ | CH₃ | |
| 22 | 4-chlorobenzoyl piperidine linked via propyl amide to thiophen-2-yl | CN | CONH₂ | CO₂CH₃ | CH₃ | |
| 23 | 2-nitrophenyl piperazine linked via butyl to pyrazol-3-yl | CH₂OH | NO₂ | CHO | CH₃ | |
| 24 | 3-chlorobenzyl amino linked via propyl to pyrazol-3-yl | CH₃ | NO₂ | COCH₃ | CH₃ | |
| 25 | 2-methoxyphenyl piperazine linked via butyl to 2-acylphenyl | CH₃ | CN | CO₂C₂H₅ | CH₃ | |

TABLE 1-continued

| Ex. No. | Cy | R² | R³ | R⁵ | R⁶ | mp °C. |
|---|---|---|---|---|---|---|
| 26 | 3-CF₃-phenyl-NH-C(O)-(CH₂)₃-N(piperazinyl)-CH₂- with 4-(pyrimidin-2-yl) | CH₃ | CONH₂ | COCH₃ | CH₃ | |
| 27 | 2-(phenyl-piperazin-1-yl-propanoyloxy)phenyl- | C₃H₇ | NO₂ | CO₂CH₂CHOHC₆H₅ | CH₃ | |
| 28 | 2-(1-methoxy-4-(2-phenoxyethylamino)butyl)phenyl- | CH₃ | NO₂ | CO₂C₃H₇ | CH₃ | |
| 29 | 2-(4-(4-(benzo[1,4]dioxin-2-ylcarbonyl)piperazin-1-yl)butylsulfinyl)phenyl- | CN | 3-oxo-tetrahydrofuran-4-yl | CO₂CH₃ | CH₃ | |
| 30 | 2-methyl-3-(N-methyl-N-(3-(4-cyclopropylpiperazin-1-yl)propyl)amino)phenyl- | CN | CN | CO₂CH₃ | CH₃ | |

TABLE 1-continued (I)

[Structure: dihydropyridine core with R², R³, R⁵, R⁶ substituents, Cy-H at 4-position, NH]

| Ex. No. | Cy | R² | R³ | R⁵ | R⁶ | mp °C. |
|---------|----|----|----|----|----|--------|
| 31 | 2-(4-(3-(4-(tetrahydrofuran-carbonyl)piperidin-1-yl)propyl)oxycarbonyl)phenyl | CH₃ | CONH₂ | CO₂C₂H₅ | CH₃ | |
| 32 | 2-(N-methyl-N-(3-(4-cyclopentylpiperazin-1-yl)propanoyl)amino)phenyl | CH₂OH | H | CO₂CH₃ | C₂H₅ | |
| 33 | 2-(4-(4-(3,4-dichlorobenzoyl)piperazin-1-yl)butylsulfinyl)phenyl | CH₃ | CN | CO₂CH₃ | CH₃ | |
| 34 | 3-chloro-2-(3-(4-phenylpiperidin-1-yl)propoxy)phenyl | NH₂ | NO₂ | CO₂CH₃ | CH₃ | |
| 35 | 2-(N-oxide-N-(4-(4-(3-nitrophenyl)piperazin-1-yl)butyl)amino)phenyl | C₂H₅ | NO₂ | CO₂CH₃ | C₂H₅ | |

TABLE 1-continued (I) structure with Cy-CH, R2, R3, R5, R6 on dihydropyridine with NH

| Ex. No. | Cy | R² | R³ | R⁵ | R⁶ | mp °C. |
|---|---|---|---|---|---|---|
| 36 | 3-nitrobenzoyl-piperidin-1-yl-CH₂CH(OH)- phenyl | CH₃ | NO₂ | COCH₃ | CH₃ | |
| 37 | 2-methoxyphenyl-piperazinyl-(CH₂)₃CH(NH₂)- phenyl | CH₃ | H | CO₂CH₃ | CH₃ | |
| 38 | pyrimidinyl-piperazinyl-(CH₂)₃-O-phenyl | CH₂OH | NO₂ | CHO | CH₃ | |
| 39 | pyridinyl-piperazinyl-CH₂CH(OH)CH₂-SO₂-phenyl | CH₃ | NO₂ | CONHC₆H₅ | CH₃ | |
| 40 | 2-methoxyphenyl-piperazinyl-(CH₂)₄-furyl | CH₃ | CONH₂ | CO₂CH₃ | CH₃ | |

TABLE 1-continued (I) [structure shown with Cy-CH, R⁵, R⁶, R³, R², N-H pyridine ring]

| Ex. No. | Cy | R² | R³ | R⁵ | R⁶ | mp °C. |
|---|---|---|---|---|---|---|
| 41 | [2-methoxyphenyl-piperazinyl-propyl-SO-2-methylphenyl] | CH₃ | [γ-thiobutyrolactone] | CO₂CH₃ | C₂H₅ | |
| 42 | [2-methoxyphenyl-piperazinyl-butyl-SO-2-methylphenyl] | CH₃ | NO₂ | CO₂CH₃ | CH₃ | |
| 43 | [2-nitrophenyl-piperazinyl-propyl-imidazolyl] | CH₃ | NO₂ | CHO | CH₃ | |
| 44 | [4-phenylpiperidinyl-propyl-NH-pyrrolyl] | CH₃ | NO₂ | CO₂CH₂CHOHC₆H₅ | CH₃ | |
| 45 | [furoyl-piperazinyl-butyl-NH-cyclohexyl] | | NO₂ | CO₂C₂H₅ | CH₃ | |

TABLE 1-continued (structure I: pyridine ring with R2, R3, R5, R6 substituents and Cy-CH group)

| Ex. No. | Cy | R² | R³ | R⁵ | R⁶ | mp °C. |
|---------|-----|------|-----|---------|-------|--------|
| 46 | furan linked to -(CH₂)-CH₂-piperazine-N-pyrimidine | CH₃ | CN | CO₂CH₃ | C₂H₅ | |
| 47 | furan linked to -C(O)- piperazine-N-C(O)-tetrahydrofuran | | thiolactone | CO₂C₃H₇ | CH₃ | |
| 48 | thiophene linked to -CH(OH)- piperidine-N-(CH₂)₃-C(O)-C₆H₄-OCH₃ | CH₃ | NO₂ | CO₂CH₃ | CH₃ | |
| 49 | pyrazole linked to -(CH₂)₄-piperazine-N-(2-chloropyridine) | C₂H₅ | CONH₂ | CO₂C₂H₅ | CH₃ | |
| 50 | pyrazole linked to -(CH₂)₄-piperidine-(2-methoxyphenyl) | | lactone | CO₂CH₃ | CH₃ | |

Footnotes for Table 1
(a) see text for spectral data.
(b) ¹H-NMR(200 MHz, CDCl₃) δ 1.44(m, 2H); 1.61(m, 8H); 2.37(s, 3H); 2.45(m, 2H); 2.51(s, 3H); 2.73(m, 2H); 3.70(s, 3H); 3.88(m, 4H); 5.32(s, 1H); 6.12(s, 2H); 6.52(m, 1H); 7.00(m, 1H); 7.17(s, 1H); 7.53(s, 1H); IR(KBr): 2943, 1707, 1616, 1490, 1436, 1225 cm⁻¹. Mass Spectrum: 527(M + 1), 555(M + 29). m.p.: 105 –108° C. HRMS: Calcd: 526.2427; Found: 526.2426;
(c) ¹H-NMR(200 MHz, CDCl₃) δ 1.68–2.05(m, 4H); 2.24(s, 3H); 2.46(t, 2H, J=7Hz); 2.54(s, 3H); 2.65(m, 4H); 3.08(m, 4H); 3.35(m, 4H); 3.61(s, 3H); 3.85(s, 3H); 6.57(s, 1H); 6.67(s, 1H); 6.83–6.99(m, 4H);

TABLE 1-continued

| Ex. No. | Cy | R² | R³ | R⁵ | R⁶ | mp °C. |
|---|---|---|---|---|---|---|

(d) ¹H-NMR(200 MHz, d₆-DMSO) ∂ 1.95(s, 4H); 2.35(s, 3H); 2.57(s, 3H); 2.89(m, 2H); 3.14–3.22(m, 6H); 3.49–3.62(m, 7H); 3.81(s, 3H); 5.76(s, 1H); 6.92–7.06(m, 4H); 7.31–7.36(m, 1H); 7.43–7.52(m, 2H); 7.87–7.90(m, 1H); 10.24(s, 1H).
(e) ¹H-NMR(200 MHz, CDCl₃) ∂ 1.56(m, 4H); 1.80(t, 2H, J=7Hz); 2.31(s, 3H); 2.48(s, 3H); 2.54(m, 6H); 3.59(s, 3H); 3.84(m, 4H); 3.95(t, 2H, J=7Hz); 5.64(m, 1H); 6.36(s, 1H); 6.50(m, 1H); 6.85(m, 2H); 7.00(d, 1H, J=2Hz); 7.14(m, 1H); 7.29(m, 1H); 7.48(s, 1H). IR(KBr): 2945, 1706, 1619, 1491, 1307, 1225 cm⁻¹. Mass Spectrum: 553(M + 1), 249, 211. m.p.: 97–111° C. HRMS: Calcd: 552.2584; Found: 552.2577
(f) ¹H-NMR(200 MHz, CDCl₃) ∂ 1.50(m, 2H); 1.91(m, 2H); 2.05(m, 4H); 2.31(m, 2H); 2.39(s, 3H); 2.62(s, 3H); 2.80(s, 3H); 3.04(m, 2H); 3.58(s, 3H); 3.62(m, 2H); 3.83(t, 2H, J=6Hz); 5.51(s, 1H); 6.81(m, 2H); 7.12(m, 1H); 7.32(m, 6H); 8.56(s, 1H). IR(KBr): 2942, 1707, 1651, 1494, 1307 1224 cm⁻¹. Mass Spectrum: 534(M + 1), 562(M + 29). m.p.: 182–6° C. HRMS: Calcd: 533.2890; Found: 533.2879;
(g) ¹H-NMR(200 MHz, CDCl₃) ∂ 1.55(m, 4H); 1.78(m, 2H); 2.43(m, 2H); 2.49(s, 3H); 2.57(m, 4H); 3.60(s, 3H); 3.65(m, 4H); 3.96(t, 2H, J=6Hz); 6.55(s, 1H); 6.77(m, 1H); 6.82(m, 1H); 6.91(d, 1H, J=10Hz); 7.11(m, 1H); 7.22(d, 1H, J=10Hz); 7.29(m, 1H). IR(KBr): 2944, 1708, 1653, 1586, 1493, 1442, 1309, 1224 cm⁻¹. Mass Spectrum: 571(M + 1), 599(M + 29). m.p.: 164–166° C.
(h) ¹H-NMR(200 MHz, CDCl₃) ∂ 1.38(d, 6H, J=6Hz); 1.51–1.83(m, 6H); 2.32(s, 3H); 2.43(m, 2H); 2.49(s, 3H); 2.60(t, 4H, J=5Hz); 3.54(t, 4H, J=5Hz); 3.60(s, 3H); 3.92(t, 2H, J=6Hz); 5.42(m, 1H); 5.62(s, 1H); 6.29(m, 1H); 6.79(d, 1H, J=9Hz); 6.81(m, 2H); 7.02(d, 1H, J=9Hz); 7.13(m, 1H); 7.27(m, 1H). IR(KBr): 3312, 2943, 1707, 1651, 1444, 1306, 1224 cm⁻¹. Mass Spectrum: 595(M + 1), 623(M + 29), 548, 563, 593. m.p.: 97–105° C. HRMS: Calcd: 594.3166; Found: 594.3153;
(i) ¹H-NMR(200 MHz, CDCl₃) ∂ 1.46–1.66(m, 4H); 1.66–1.86(m, 2H); 2.31(s, 3H); 2.36–2.59(m, 6H); 2.46(s, 3H); 3.50–3.86(m, 4H); 3.60(s, 3H); 3.96(m, 4H); 3.96(s, 3H); 3.96(t, 2H, J=7Hz); 4.33(dd, 1H, J=8, 12Hz); 4.50(dd, 1H, J=2, 12Hz); 4.85(dd, 1H, J=2, 8Hz); 5.66(s, 1H); 6.22(s, 1H); 6.73–6.96(m, 6H); 7.07–7.26(m, 2H). IR(KBr): 3629, 3309, 2943, 2867, 1706, 1648, 1494, 1307, 1269, 1225, 1101, 1016, 751 cm⁻¹. Mass Spectrum: 621(M + 1), 649(M + 29). m.p.: 80–84° C.
(j) ¹H-NMR(200 MHz, CDCl₃) ∂ 1.52–1.66(m, 4H); 1.78–1.85(m, 2H); 2.32(s, 3H); 2.42(m, 2H); 2.48(s, 3H); 2.58(t, 4H, J=5Hz); 3.60(s, 3H); 3.61(m, 4H); 3.96(m, 2H, J=7Hz); 5.64(s, 1H); 6.16(s, 1H); 6.79(m, 1H); 6.83(m, 1H); 7.12(m, 1H); 7.26(m, 1H); 7.85(d, 1H, J=3Hz); 8.07(m, 1H); 8.14(d, 1H, J=1Hz). IR(KBr): 3310, 3078, 2944, 1707, 1492, 1380, 1313, 1222, 1016 cm⁻¹. Mass Spectrum: 537(M + 1), 565(M + 29). m.p.: 66–69° C. HRMS: Calcd: 536.2747; Found: 536.2735.
(k) ¹H-NMR(200 MHz, CDCl₃) ∂ 1.03(t, 3H, J=6Hz); 1.50–1.66(m, 4H); 1.73–1.86(m, 4H); 2.30(s, 3H); 2.43(m, 2H); 2.46(s, 3H); 2.53(m, 4H); 3.61(m, 4H); 3.63(s, 3H); 3.96(t, 2H, J=7Hz); 4.24(t, 2H, J=6Hz); 5.66(s, 1H); 5.82(s, 1H); 6.40(s, 1H); 6.79–6.89(m, 2H); 7.07–7.20(m, 1H); 7.28(m, 1H); 8.60(s, 1H). IR(KBr): 3316, 3094, 2936, 1708, 1593, 1540, 1493, 1380, 1306, 1220, 1013, 750 cm⁻¹. Mass Spectrum: 595(M + 1), 623(M + 29). HRMS: Calcd: 593.3087; Found: 593.3031.

TABLE 2

(I)

| Ex. No. | Cy | R² | R³ | R⁵ | R⁶ | mp °C. |
|---|---|---|---|---|---|---|
| 51 | benzofurazan-4-yl | CH₃ | NO₂ | —CO₂(CH₂)₄—N(piperazinyl)-(2-methoxyphenyl) | CH₃ | glassy solid[a] |
| 52 | pyridin-3-yl | CH₃ | NO₂ | —CO₂(CH₂)₄—N(piperazinyl)-(2-methoxyphenyl) | CH₃ | 155–160[b] |
| 53 | pyridin-3-yl | CH₃ | NO₂ | —CO₂(CH₂)₄—N(piperazinyl)-(pyrimidin-2-yl) | CH₃ | 155–160[c] (dec) |
| 54 | benzofurazan-4-yl | CH₃ | NO₂ | —CO₂(CH₂)₄—N(piperazinyl)-(pyrimidin-2-yl) | CH₃ | 77–80[d] |
| 55 | furan-3-yl | CH₃ | NO₂ | —CO₂(CH₂)₂—N(piperazinyl)-(2-methoxyphenyl) | CH₃ | 51–61[e] |
| 56 | furan-3-yl | CH₃ | NO₂ | —CO₂(CH₂)₂—N(piperazinyl)-(pyrimidin-2-yl) | CH₃ | 50–54[f] |
| 57 | 1-methylpyrrol-2-yl | CH₃ | NO₂ | —CO₂(CH₂)₄—N(piperazinyl)-(2-methoxyphenyl) | CH₃ | 52–56[g] |
| 58 | 1-methylpyrrol-2-yl | CH₃ | NO₂ | —CO₂(CH₂)₄—N(piperazinyl)-(pyrimidin-2-yl) | CH₃ | 51–55[h] |
| 59 | furan-2-yl | CH₃ | NO₂ | —CO₂(CH₂)₂—N(piperazinyl)-(2-methoxyphenyl) | CH₃ | 59–63[i] |

TABLE 2-continued $$\text{(I)}$$

| Ex. No. | Cy | R² | R³ | R⁵ | R⁶ | mp °C. |
|---|---|---|---|---|---|---|
| 60 | 2-furyl | CH₃ | NO₂ | —CO₂(CH₂)₂—N(piperazinyl)-pyrimidin-2-yl | CH₃ | 65–72[j] |
| 61 | pyridin-3-yl | CH₃ | NO₂ | —CO₂(CH₂)₂—N(piperazinyl)-(2-methoxyphenyl) | CH₃ | 160–178[k] |
| 62 | pyridin-3-yl | CH₃ | NO₂ | —CO₂(CH₂)₂—N(piperazinyl)-pyrimidin-2-yl | CH₃ | 197–200[l] (dec) |
| 63 | thien-2-yl | CH₃ | NO₂ | —CO₂(CH₂)₄—N(piperazinyl)-(2-methoxyphenyl) | CH₃ | 57–62[m] |
| 64 | thien-2-yl | CH₃ | NO₂ | —CO₂(CH₂)₄—N(piperazinyl)-pyrimidin-2-yl | CH₃ | glassy solid[n] |
| 65 | thien-3-yl | CH₃ | NO₂ | —CO₂(CH₂)₂—N(piperazinyl)-(2-methoxyphenyl) | CH₃ | glassy solid[o] |
| 66 | thien-3-yl | CH₃ | NO₂ | —CO₂(CH₂)₂—N(piperazinyl)-pyrimidin-2-yl | CH₃ | 58–63[p] |
| 67 | fur-3-yl | CH₃ | NO₂ | —CO₂(CH₂)₄—N(piperazinyl)-(2-methoxyphenyl) | CH₃ | glassy solid[q] |
| 68 | 1-methylpyrrol-2-yl | CH₃ | NO₂ | —CO₂(CH₂)₄—N(piperazinyl)-pyrimidin-2-yl | CH₃ | glassy solid[r] |
| 69 | 2-furyl | CH₃ | NO₂ | —CO₂(CH₂)₄—N(piperazinyl)-(2-methoxyphenyl) | CH₃ | glassy solid[s] |

TABLE 2-continued

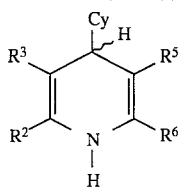

(I)

| Ex. No. | Cy | $R^2$ | $R^3$ | $R^5$ | $R^6$ | mp °C. |
|---|---|---|---|---|---|---|
| 70 | furan-2-yl | $CH_3$ | $NO_2$ | $-CO_2(CH_2)_4-N\underset{}{\bigcirc}N-\underset{N}{\overset{N}{\bigcirc}}$ | $CH_3$ | glassy solid[t] |
| 71 | thiophen-3-yl | $CH_3$ | $NO_2$ | $-CO_2(CH_2)_4-N\underset{}{\bigcirc}N-\text{(2-methoxyphenyl)}$ | $CH_3$ | glassy solid[u] |
| 72 | thiophen-3-yl | $CH_3$ | $NO_2$ | $-CO_2(CH_2)_4-N\underset{}{\bigcirc}N-\underset{N}{\overset{N}{\bigcirc}}$ | $CH_3$ | glassy solid[v] |
| 73 | thiophen-2-yl | $CH_3$ | $NO_2$ | $-CO_2(CH_2)_2-N\underset{}{\bigcirc}N-\underset{N}{\overset{N}{\bigcirc}}$ | $CH_3$ | 62–66[w] |
| 74 | thiophen-2-yl | $CH_3$ | CN | $-CO_2(CH_2)_2-N\underset{}{\bigcirc}N-\text{(2-methoxyphenyl)}$ | $CH_3$ | 62–65[x] |
| 75 | benzofurazan-4-yl | $CH_3$ | $NO_2$ | $-CO_2(CH_2)_2-N\underset{}{\bigcirc}N-\text{(2-methoxyphenyl)}$ | $CH_3$ | glassy solid[y] |
| 76 | benzofurazan-4-yl | $CH_3$ | $NO_2$ | $-CO_2(CH_2)_2-N\underset{}{\bigcirc}N-\underset{N}{\overset{N}{\bigcirc}}$ | $CH_3$ | glassy solid[z] |
| 77 | 1-methylpyrrol-2-yl | $CH_3$ | $NO_2$ | $-CO_2(CH_2)_2-N\underset{}{\bigcirc}N-\text{(2-methoxyphenyl)}$ | $CH_3$ | glassy solid[aa] |
| 78 | 1-methylpyrrol-2-yl | $CH_3$ | $NO_2$ | $-CO_2(CH_2)_2-N\underset{}{\bigcirc}N-\underset{N}{\overset{N}{\bigcirc}}$ | $CH_3$ | glassy solid[bb] |

TABLE 2-continued

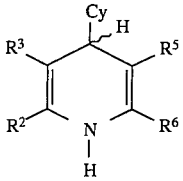
(I)

| Ex. No. | Cy | R² | R³ | R⁵ | R⁶ | mp °C. |
|---|---|---|---|---|---|---|
| 79 | 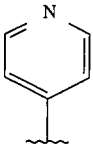 | CH₃ | NO₂ | 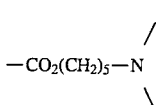 —CO₂(CH₂)₅—N∩N—CO—⟨C₆H₄⟩—Cl | CH₃ | |
| 80 | 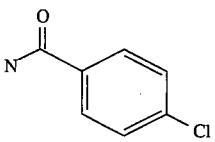 | CH₃ | CONH₂ | 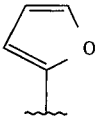 —CO₂(CH₂)₄—N(piperidine)—CO—⟨C₆H₄⟩—OCH₃ | CH₃ | |
| 81 | 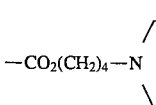 | CH₃ | 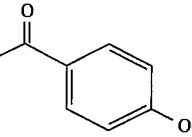 | —CO₂(CH₂)₄—N∩N—cyclopentyl | CH₃ | |
| 82 | 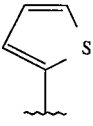 | CH₃ | NO₂ | —CONH(CH₂)₄NH(CH₂)₂—S—⟨C₆H₄⟩—Cl | CN | |
| 83 | 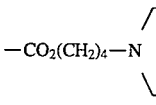 | CH₂OH | NO₂ | 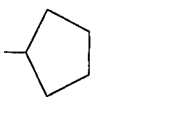 —CO₂(CH₂)₂—N∩N—(pyridin-4-yl) | CH₃ | |
| 84 | 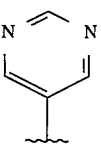 | CH₃ | H | 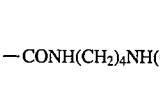 —CO₂(CH₂)₄—N∩N—CO—CH(CH₃)—CH₂—O—⟨benzo-dioxole⟩ | CH₃ | |
| 85 | 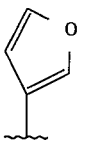 | CH₃ | CN | 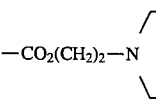 —CO₂(CH₂)₃—N(piperidine)—⟨2-Cl-C₆H₄⟩ | CH₃ | |
| 86 | 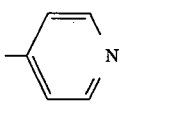 | CH₃ | H | 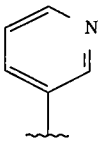 —CO₂(CH₂)₅—N∩N—⟨2-OCH₃-C₆H₄⟩ | CN | |
| 87 | 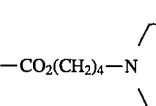 | 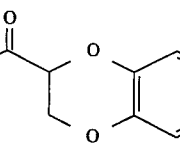 | | —CONH(CH₂)₂—N∩N—(pyrazin-2-yl) | CH₃ | |

TABLE 2-continued
(I)
| Ex. No. | Cy | R² | R³ | R⁵ | R⁶ | mp °C. |
|---|---|---|---|---|---|---|
| 88 | 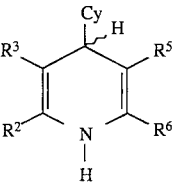 | C₂H₅ | NO₂ | 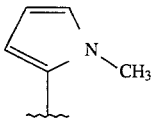 | CH₃ | |
| 89 | 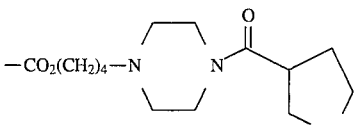 | C₃H₇ | NO₂ | 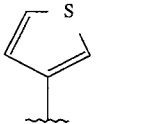 | C₃H₇ | |
| 90 | 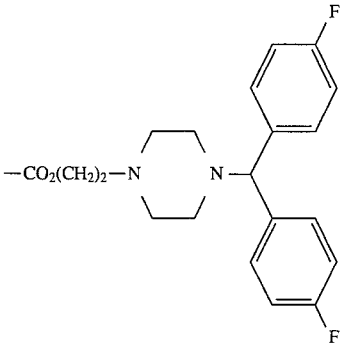 | CH₂OH | CN | 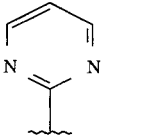 | CH₃ | |
| 91 | 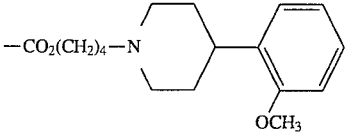 | CH₃ | NO₂ | 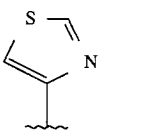 | CH₂OH | |
| 92 | 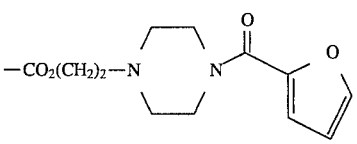 | 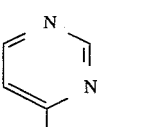 | | 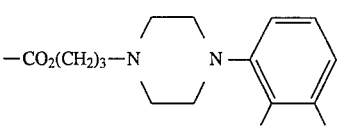 | CN | |
| 93 | 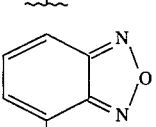 | CH₂OH | CN | 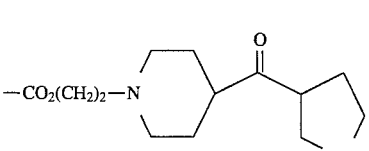 | CH₃ | |
| 94 | 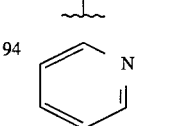 | CH₃ | NO₂ | 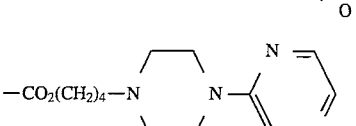 | CH₃ | |
| 95 | 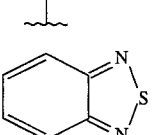 | C₂H₅ | NO₂ | 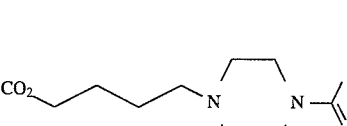 | C₂H₅ | |

TABLE 2-continued

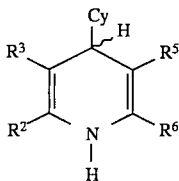

(I)

| Ex. No. | Cy | R² | R³ | R⁵ | R⁶ | mp °C. |
|---|---|---|---|---|---|---|
| 96 | 3-pyridyl | CN | CN | -CONH-(CH₂)₃-N(piperazine)N-CO-(2-furyl) | CH₃ | |
| 97 | 5-pyrimidinyl | CH₃ | NO₂ | -CO₂-(CH₂)₂-N(piperazine)N-(2-pyridyl) | CH₃ | |
| 98 | 2-furyl | | -C(=O)-S (thiolactone) | -CO₂-(CH₂)₃-N(piperazine)N-CO-(3-NCH₃-2-furyl) | C₂H₅ | |
| 99 | 2-thienyl | CH₂OH | NO₂ | -CO₂-(CH₂)₄-N(piperazine)N-(4-OPr-pyrimidin-2-yl) | CH₂OH | |
| 100 | N-methyl-2-pyrrolyl | CH₃ | CONH₂ | -CONH-(CH₂)₃-N(piperazine)N-(4,6-dimethoxy-1,3,5-triazin-2-yl) | CH₃ | |

Footnotes for Table 2
(a) ¹H-NMR (200 MHz, CDCl₃) ∂ 1.55 (m, 4H); 2.35 (s, 3H); 2.38 (m, 2H); 2.54 (s, 3H); 2.63 (m, 4H); 3.10 (m, 4H); 3.87 (s, 3H); 4.08 (t, 2H, J=6Hz); 5.81 (s, 1H); 6.95 (m, 3H); 7.35–7.50 (m, 4H); 7.69 (d, 1H, J=9Hz). Mass Spectrum: 563 (M + 1), 591 (M + 29).
(b) ¹H-NMR (200 MHz, CDCl₃) ∂ 1.50 (m, 2H); 1.61 (m, 2H); 2.38 (s, 3H); 2.40 (m, 1H); 2.53 (s, 3H); 2.63 (m, 4H); 3.10 (m, 4H); 3.87 (s, 3H); 4.08 (t, 2H, J=6Hz); 5.38 (s, 1H); 6.85–7.08 (m, 4H); 7.25 (m, 1H); 7.39 (s, 1H); 7.74 (d, 1H, J=8Hz); 8.42 (d, 1H, j=3Hz); 8.50 (d, 1H, J=2Hz). IR (KBr): 2940, 2816, 1705, 1646, 1501, 1466, 1310, 1272, 1225 cm⁻¹. Mass Spectrum: 522 (M + 1), 550 (M + 29), 247 (C₁₅H₂₃N₂O). m.p.: 155–160° C.
(c) see text for spectral data
(d) ¹H-NMR (200 MHz, CDCl₃) ∂ 1.53 (m, 2H); 1.61 (m, 2H); 2.35 (m, 2H); 2.37 (s, 3H); 2.46 (t, 4H, J=5Hz); 2.55 (s, 3H); 3.82 (t, 4H, J=5Hz); 4.07 (t, 2H, J=7Hz); 5.81 (s, 1H); 6.50 (t, 1H, J=5Hz); 6.53 (s, 1H); 7.34 (dd, 1H, J=6, 9Hz); 7.46 (d, 1H, J=6Hz); 7.68 (d, 1H, J=9Hz); 8.31 (d, 2H, J=5Hz). IR (KBr): 3500, 3308, 3212, 3084, 2946, 1705, 1587, 1548, 1498, 1449, 1359, 1311, 1262, 1221, 1105, 1014, 983, 797, 752 cm⁻¹. Mass Spectrum: 535 (M + 1), 563 (M + 29). m.p.: 77–80° C.
(e) ¹H-NMR (200 MHz, CDCl₃) ∂ 2.39 (s, 3H); 2.51 (s, 3H); 2.71 (m, 6H); 3.05 (m, 4H); 3.87 (s, 3H); 4.25–4.39 (m, 2H); 5.43 (s, 1H); 6.32 (s, 1H); 6.84–7.03 (m, 5H); 7.29 (m, 2H). IR (KBr): 3510, 3315, 3230, 3090, 2940, 2830, 1708, 1650, 1500, 1450, 1385, 1320, 1280, 1240, 1150, 1110, 1010, 750 cm⁻¹. Mass Spectrum: 483 (M + 1), 511 (M + 29). m.p.: 57–61° C. HRMS: Calcd: 482.2165; Found: 482.2154
(f) ¹H-NMR (200 MHz, CDCl₃) ∂ 2.39 (s, 3H); 2.52 (s, 3H); (m, 4H); 2.67 (m, 2H); 3.80 (t, 4H, J=5Hz); 4.20 (m, 1H); 4.26 (m, 1H); 5.42 (s, 1H); 6.08 (s, 1H); 6.49 (t, 1H, J=5Hz); 7.28 (m, 2H); 8.31 (d, 2H, J=5Hz). IR (KBr): 3500, 3302, 3100, 2950, 2820, 1700, 1685, 1653, 1586, 1548, 1497, 1450, 1360, 1313, 1260, 1229, 1151, 1106, 1017, 984, 797 cm⁻¹. Mass Spectrum: 455 (M + 1), 483 (M + 29). m.p.: 50–54° C. HRMS: Calcd: 454.1864; Found: 454.1969
(g) ¹H-NMR (200 MHz, CDCl₃) ∂ 1.51–1.70 (m, 4H); 2.37 (s, 3H); 2.39 (m, 2H); 2.51 (s, 3H); 2.61 (m, 4H); 3.09 (m, 4H); 3.85 (s, 3H); 3.87 (s, 3H); 4.14 (m, 2H); 5.29 (s, 1H); 5.86 (m, 1H); 5.96 (m, 2H); 6.42 (t, 1H J=2Hz); 6.84–7.00 (m, 4H). IR (KBr): 3500, 3310, 3093, 2943, 2818, 1700, 1684, 1652, 1500, 1456, 1380, 1313, 1221, 1102, 1013, 814, 750 cm⁻¹. Mass Spectrum: 524 (M + 1), 552 (M + 29). m.p.: 52–56° C.
(h) ¹H-NMR (200 MHz, CDCl₃) ∂ 1.48–1.66 (m, 4H); 2.35 (m, 2H); 2.37 (s, 3H); 2.46 (m, 4H); 2.52 (s, 3H) 3.80 (m, 4H); 3.84 (s, 3H); 4.12 (m, 2H); 5.28 (s, 1H); 5.86 (m, 1H); 5.97 (m, 2H); 6.42 (m, 1H); 6.47 (t, 1H, J=5Hz); 8.32 (d, 2H, J=5Hz). IR (KBr): 3500, 3310, 3210, 3092, 2943, 2851, 1700, 1684, 1653, 1586, 1549, 1497, 1448, 1388, 1360, 1311, 1290, 1262, 1220, 1101, 1013, 983, 797, 703 cm⁻¹. Mass Spectrum: 496 (M + 1), 524 (M + 29). m.p.: 51–55° C.
(i) ¹H-NMR (200 MHz, CDCl₃) ∂ 2.40 (s, 3H); 2.53 (s, 3H); 2.66–2.79 (m, 6H); 3.00–3.17 (m, 4H); 3.86 (s, 3H); 4.17–4.43 (m, 2H); 5.63 (s, 1H); 6.07 (s, 1H); 6.18 (m, 1H); 6.26 (m, 1H); 6.82–7.00 (m, 4H); 7.23 (m, 1H). IR (KBr): 3500, 3310, 3230, 3075, 2942, 2822, 1701, 1684, 1652, 1500, 1456, 1381, 1316, 1272, 1225, 1150, 1103, 1011, 800, 747 cm⁻¹. Mass Spectrum: 483 (M + 1), 511 (M + 29). m.p.:59–63° C. HRMS: Calcd: 482.2165; Found: 484.2164

TABLE 2-continued

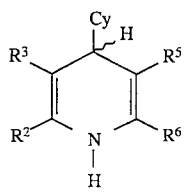

(I)

| Ex. No. | Cy | R² | R³ | R⁵ | R⁶ | mp °C. |
|---|---|---|---|---|---|---|

(j) ¹H-NMR (200 MHz, CDCl₃) ∂ 2.40 (s, 3H); 2.53 (m, 4H); 2.54 (s, 3H); 2.68 (t, 2H, J=6Hz); 3.80 (m, 4H); 4.23–4.35 (m, 2H); 5.62 (s, 1H); 6.09 (s, 1H); 6.15 (d, 1H, J=3Hz); 6.25 (m, 1H); 6.49 (t, 1H, J=5Hz); 7.23 (d, 1H, J=2Hz); 8.30 (d, 2H, J=5Hz). IR (KBr): 3546, 3310, 3094, 2941, 2822, 1706, 1648, 1586, 1548, 1490, 1449, 1360, 1314, 1261, 1224, 1152, 1102, 1010, 982, 797, 739 cm⁻¹. Mass Spectrum: 455 (M + 1), 483 (M + 29). m.p.: 65–72° C. HRMS: Calcd: 454.1964; Found: 454.1969

(k) ¹H-NHR (200 MHz, CDCl₃) ∂ 2.40 (s, 3H); 2.54 (s, 3H); 2.64 (m, 6H); 3.05 (m, 4H); 3.87 (s, 3H); 4.22 (t, 2H, J=6Hz); 5.42 (s, 1H); 6.84–7.00 (m, 4H); 7.08 (m, 1H); 7.21 (m, 1H); 7.77 (d, 1H, J=8Hz); 8.42 (m, 1H); 8.52 (d, 1H, J=2Hz). IR (KBr): 3500, 3296, 3174, 3057, 2933, 2829, 1705, 1642, 1592, 1500, 1450, 1377, 1309, 1270, 1222, 1145, 1101, 1021, 753 cm⁻¹. Mass Spectrum: 494 (M + 1) 522 (M + 29). m.p.: 160–178° C.

(l) ¹H-NMR (200 MHz, CDCl₃) ∂ 2.39 (s, 3H); 2.48 (m, 4H); 2.53 (s, 3H); 2.60 (t, 2H, J=6Hz); 3.77 (m, 4H); 4.21 (m, 2H); 5.41 (s, 1H); 6.49 (t, 1H, J=5Hz); 7.22 (m, 2H); 7.76 (d, 1H, J=8Hz); 8.30 (d, 2H, J=5Hz); 8.41 (m, 1H); 8.52 (d, 1H, J=2Hz). IR (KBr): 3500, 3190, 3061, 2936, 1682, 1587, 1546, 1506, 1307, 1234, 1105, 1016, 984, 780 cm⁻¹. Mass Spectrum: 466 (M + 1), 494 (M + 29). m.p.: 197–200° C. (dec).

(m) ¹H-NMR (200 MHz, CDCl₃) ∂ 1.36–1.69 (m, 4H); 2.38 (m, 2H); 2.40 (s, 3H); 2.53 (s, 3H); 2.62 (m, 4H); 3.08 (m, 4H); 3.87 (s, 3H); 4.14 (m, 2H); 5.77 (s, 1H); 6.08 (s, 1H); 6.82–7.03 (m, 4H); 6.86 (m, H); 7.09 (m, 1H). IR (KBr): 3500, 3304, 3065, 2942, 2817, 1704, 1642, 1501, 1314, 1272, 1228, 1103, 749 cm⁻¹. Mass Spectrum: 527 (M + 1), 555 (M + 29). m.p.: 57–62° C.

(n) ¹H-NMR (200 MHz, CDCl₃) ∂ 1.51 (m, 2H); 1.66 (m, 2H); 2.36 (m, 2H); 2.40 (s, 3H); 2.46 (m, 4H); 2.53 (s, 3H); 3.82 (m, 4H); 4.16 (m, 2H); 5.76 (s, 1H); 6.43 (s, 1H); 6.46 (m, 1H); 6.87 (m, 2H); 7.10 (m, 1H); 8.30 (m, 2H). IR (KBr): 3500, 3306, 3068, 2939, 1706, 1586, 1548, 1492, 1359, 1312, 1226, 1012, 982, 795 cm⁻¹. Mass Spectrum: 499 (M + 1), 527 (M + 29).

(o) ¹H-NMR (200 MHz, CDCl₃) ∂ 2.40 (s, 3H); 2.52 (s, 3H); 2.69 (m, 6H); 3.05 (m, 4H); 3.87 (s, 3H); 4.22–4.33 (m, 2H); 5.60 (s, 1H); 6.06 (s, 1H); 6.84–7.00 (m, 3H); 7.03 (m, 2H); 7.12 (m, 2H). IR (KBr): 3500, 3309, 3096, 2941, 2822, 1703, 1500, 1314, 1226, 1104, 1015, 749 cm⁻¹. Mass Spectrum: 499 (M + 1), 527 (M + 29).

(p) ¹H-NMR (200 MHz, CDCl₃) ∂ 2.40 (s, 3H); 2.46 (m, 4H); 2.52 (s, 3H); 2.64 (t, 2H, J=6Hz,); 3.78 (m, 4H); 4.18 (m, 1H); 4.34 (m, 1H); 5,59 (s, 1H); 6.01 (s, 1H); 6.48 (t, 1H, J=5Hz); 7.03 (m, 1H); 7.09 (s, 1H); 7.17 (m, 1H); 8.29 (d, 2H, J=5Hz). IR (KBr): 3500, 3312, 3094, 2943, 1703, 1586, 1548, 1492, 1360, 1311, 1262, 1225, 1104, 1015, 983 cm⁻¹. Mass Spectrum: 471 (M + 1), 499 (M + 29). m.p.: 58–63° C. HRMS: Calcd: 470.1736; Found: 470.1731

(q) ¹H-NMR (200 MHz, CDCl₃) ∂ 1.49–1.61 (m, 2H); 1.62–1.73 (m, 2H); 2.37 (s, 3H); 2.44 (m, 2H); 2.5 (s, 3H); 2.62 (m, 4H); 3.10 (m, 4H); 3.87 (m, 3H); 4.16 (m, 2H); 5.41 (s, 1H); 6.22 (s, 1H); 6.28 (s, 1H); 6.84–7.04 (m, 4H); 7.27 (m, 2H); IR (KBr): 3310, 2944, 2818, 1703, 1652, 1500, 1315, 1230, 1106, 1017, 750 cm⁻¹. Mass Spectrum: 511 (M + 1), 539 (M + 29).

(r) ¹H-NMR (200 MHz, CDCl₃) ∂ 1.50–1.62 (m, 2H); 1.68 (m, 2H); 2.33–2.44 (m, 2H); 2.38 (s, 3H); 2.48 (m,4H); 2.50 (s, 3H); 3.82 (t, 4H, J=5Hz); 4.07–4.19 (m, 2H); 5.41 (s, 1H); 6.28 (d, 1H, J=1Hz); 6.36 (s, 1H); 6.48 (t, 1H, J=5Hz); 7.24 (s, 1H); 8.29 (d, 2H, J=5Hz). IR (KBr): 3312, 2950, 1702, 1586, 1548, 1492, 1359, 1313, 1229, 1106, 1015, 753 cm⁻¹. Mass Spectrum: 482 (M⁺).

(s) ¹H-NMR (200 MHz, CDCl₃) ∂ 1.52–1.73 (m, 4H); 2.39 (s, 3H); 2.42 (m, 2H); 2.54 (s, 3H); 2.64 (m, 4H); 3.10 (m, 4H); 3.87 (s, 3H); 4.15 (m, 2H); 5.61 (s, 1H); 6.10 (d, 1H, J=3Hz); 6.17 (s, 1H); 6.24 (m, 1H); 6.84–7.01 (m, 4H); 7.21 (d, 1H, J=2Hz). IR (film); 3312, 2945, 2819, 1703, 1500, 1316, 1230, 1011, 750 cm⁻¹. Mass Spectrum: (M + 1), (M + 29). HRMS: Calcd: 510.2478; Found: 510.2466

(t) ¹H-NMR (200 MHz, CDCl₃) ∂ 1.54 (m, 2H); 1.60–1.71 (m, 2H); 2.35–2.42 (m, 2H); 2.39 (s, 3H); 2.48 (t, 4H, J=5Hz); 2.54 (s, 3H); 3.82 (t, 4H, J=5Hz); 4.15 (m, 2H); 5.61 (s, 1H); 6.10 (d, 1H, J=3Hz); 6.16 (s, 1H); 6.24 (t, 1H, J=3Hz); 6.47 (t, 1H, J=5Hz); 7.22 (s, 1H); 8.30 (d, 2H, J=5Hz). IR (film): 3314, 2947, 1704, 1586, 1548, 1494, 1359, 1315, 1224, 1011, 984, 752 cm⁻¹. Mass Spectrum: 483 (M + 1), 511 (M + 29).

(u) ¹H-NMR (200 MHz, CDCl₃) ∂ 1.54 (m, 2H); 1.65 (m, 2H); 2.33 (s, 3H); 2.40 (t, 2H, J=7Hz); 2.47 (s, 3H); 2.62 (s, 4H); 3.09 (m, 4H); 3.85 (s,3 H); 4.12 (d, 2H<, J=5Hz); 5.56 (s, 1H); 6.84–7.01 (m, 4H); 7.03 (m, 2H); 7.15 (m, 1H); 7.36 (s, 1H). IR (film): 3314, 2943, 2818, 1702, 1500, 1312, 1226, 1014, 751 cm⁻¹. Mass Spectrum: 527 (M + 1), 555 (M + 29).

(v) ¹H-NMR (200 MHz, CDCl₃) ∂ 1.50 (m, 2H); 1.64 (m, 2H); 2.35 (t, 2H, J=7Hz); 2.40 (s, 3H); 2.46 (t, 4H, J=5Hz); 2.52 (s, 3H); 3.82 (t, 4H, J=5Hz); 4.12 (m, 2H); 5.57 (s, 1H); 5.99 (s, 1H); 6.48 (t, 1H, J=5Hz); 7.01 (m, 2H); 7.17 (m, 1H); 8.30 (d, 2H, J=5Hz). IR (KBr): 3314, 3097, 2946, 1702, 1586, 1547, 1492, 1359, 1312, 1226, 1014, 983, 796 cm⁻¹. Mass Spectrum: 499 (M + 1), 527 (M + 29). HRMS: Calcd: 498.2049; Found: 498.2060.

(w) ¹H-NMR (200 MHz, CDCl₃) ∂ 2.43 (s, 3H); 2.48 (m, 4H); 2.53 (s, 3H); 2.66 (t, 2H, J=5Hz); 3.77 (m, 4H); 4.23 (m, 1H); 4.33 (m, 1H); 5.78 (s, 1H); 6.00 (s, 1H); 6.48 (t, 1H, J=5Hz); 6.88 (m, 1H); 6.92 (d, 1H, J=2Hz); 7.11 (m, 1H); 8.29 (d, 2H, J=5Hz). IR (KBr): 3308, 3089, 2941, 1705, 1586, 1548, 1491, 1360, 1311, 1227, 1014, 983 cm⁻¹. Mass Spectrum: 471 (M + 1), 499 (M + 29). m.p.: 63–66° C. HRMS: Calcd: 470.1736; Found: 470.1735.

(x) ¹H-NMR (200 MHz, CDCl₃) ∂ 2.43 (s, 3H); 2.53 (s, 3H); 2.66 (m, 4H); 2.70 (m, 2H); 3.05 (m, 4H); 3.87 (m, 3H); 4.26–4.34 (m, 2H); 5.79 (s, 1H); 6.03 (s, 1H); 6.84–7.03 (m, 6H); 7.11 (m, 1H). IR (KBr): 3311, 3068, 2940, 2821, 1705, 1500, 1381, 1314, 1230, 1015, 750 cm⁻¹. Mass Spectrum: 499 (M + 1), (M + 29). m.p.: 62–65° C. HRMS: Calcd: 498.1936; Found: 498.1942.

(y) ¹H-NMR (200 MHz, CDCl₃) ∂ 2.38 (s, 3H); 2.56 (s, 3H); 2.57–2.67 (m, 6H); 3.03 (m, 4H); 3.87 (s, 3H); 4.19 (m, 2H); 5.82 (s, 1H); 6.30 (s, 1H); 6.85–7.04 (m, 4H); 7.34 (m, 1H); 7.52 (d, 1H, J=7Hz); 7.68 (d, 1H, J=9Hz). IR (KBr): 3323, 3094, 2941, 2820, 1707, 1500, 1312, 1223, 1015, 750 cm⁻¹. Mass Spectrum: 535 (M + 1), 563 (M + 29). HRMS: Calcd: 534.2227; Found: 534.2219.

(z) ¹H-NMR (200 MHz, CDCl₃) ∂ 2.38 (s, 3H); 2.49 (t, 4H, J=5Hz); 2.56 (s, 3H); 2.61 (m, 2H); 3.77 (t, 4H, J=5Hz); 4.20 (m, 2H); 5.82 (s, 1H); 6.25 (s, 1H); 6.49 (t, 1H, J=5Hz); 7.34 (dd, 1H, J=7, 9Hz); 7.50 (d, 1H, J=7Hz); 7.69 (d, 1H, J=9Hz); 8.31 (d, 2H, J=5Hz). IR (KBr): 3330, 3100, 2950, 2830, 1710, 1585, 1545, 1500, 1360, 1305, 1230, 1100, 1012, 980, 748 cm⁻¹. Mass Spectrum: 507 (M + 1), 535 (M + 29).

(aa) see text for spectral data.

(bb) ¹H-NMR (200 MHz, CDCl₃) ∂ 2.38 (s, 3H); 2.49 (t, 4H, J=5Hz); 2.52 (s, 3H); 2.62 (t, 2H, J=6Hz); 3.78 (t, 4H, J=5Hz); 3.86 (s, 3H); 4.26 (m, 2H); 5.30 (s, 1H); 5.87 (dd, 1H, J=2, 3Hz); 5.92 (s, 1H); 5.97 (t, 1H, J=3Hz); 6.42 (t, 1H, J=2Hz); 6.49 (t, 1H, J=5Hz); 8.30 (d, 2H, J=5Hz). IR (KBr): 3319, 3096, 2941, 2850, 1704, 1586, 1548, 1492, 1360, 1310, 1221, 1102, 1014, 983 cm⁻¹. Mass Spectrum: 468 (M + 1), 496 (M + 29). HRMS: Calcd: 467.2281; Found: 467.2267.

UTILITY

The compounds of this invention have been found to possess both $Ca^{2+}$ channel activity, preferably $Ca^{2+}$ agonist activity, and alpha₁-antagonist activity. These pharmacological properties of the compounds of this invention were evaluated in the following pharmacological experiments.

Determination of Affinity for alpha₁-Adrenoceptors

The [³H]-prazosin binding assay was carried out according to the method described by Timmermans, P. B. M. W. M., Schoop, A. M. C., and Van Zwieten, P. A., *Biochem. Pharmacol.*, 31, 899–905, (1982). The reaction mixture contained partially purified rat brain membranes (source of alpha₁-adrenoceptors), 0.2 nM [³H]-prazosin with or without potential displacer in Tris buffer. The mixture was incubated for 60 minutes at 25° C. and subsequently terminated by rapid filtration through glass fiber-filter. Receptor-bound [$^3$H]-prazosin trapped in the filter was quantitated by scintillation counting. The inhibitory concentration (IC$_{50}$) of potential displacer which gives 50% displacement of the total specifically bound [$^3$H]-prazosin is presented as a measure of the affinity of such compound for the alpha$_1$-adrenoceptor.

Determination of Affinity for Calcium Channels

[$^3$H]-Nitrendipine binding assay was carried out according to the method described by G. T. Bolger, et al., *Biochem. Biophys. Res. Comm.*, 104, 1604–1609, (1982). The reaction mixture contained rat cardiac microsomes (source of Ca$^{2+}$ channels), 0.5 nM [$^3$H]-nitrendipine with or without potential displacer in Tris buffer. The mixture was incubated for 60 minutes at 25° C. and subsequently terminated by rapid filtration through a glass fiber-filter. Membrane-bound [$^3$H]-nitrendipine trapped in the filter was quantitated by scintillation counting. The inhibitory concentration (IC$_{50}$) of potential displacer which gives 50% displacement of the total specifically bound [$^3$H]-nitrendipine is presented as a measure of the affinity of such compound for the Ca$^{2+}$ channel.

The results from the above two in vitro assays are summarized in Table 3.

TABLE 3

Binding Affinity Data for Calcium and Alpha$_1$-adrenoceptors

| Example No. | [$^3$H]-Nitrendipine binding IC$_{50}$ [M] | [$^3$H]-Prazosin binding IC$_{50}$ [M] |
|---|---|---|
| 1 | $6.0 \times 10^{-7}$ | $1.3 \times 10^{-7}$ |
| 2 | $1.5 \times 10^{-6}$ | $1.9 \times 10^{-6}$ |
| 3 | $2.4 \times 10^{-7}$ | $6.3 \times 10^{-8}$ |
| 4 | $8.9 \times 10^{-7}$ | $2.0 \times 10^{-8}$ |
| 5 | $6.8 \times 10^{-7}$ | $2.2 \times 10^{-6}$ |
| 6 | $3.6 \times 10^{-7}$ | $9.0 \times 10^{-7}$ |
| 7 | $6.5 \times 10^{-7}$ | $1.9 \times 10^{-6}$ |
| 8 | $5.8 \times 10^{-7}$ | $1.5 \times 10^{-5}$ |
| 9 | $9.5 \times 10^{-7}$ | $5.2 \times 10^{-6}$ |
| 10 | $1.2 \times 10^{-6}$ | $7.2 \times 10^{-6}$ |
| 11 | $3.6 \times 10^{-7}$ | $5.3 \times 10^{-6}$ |
| 51 | $1.1 \times 10^{-7}$ | $1.2 \times 10^{-7}$ |
| 52 | $3.9 \times 10^{-6}$ | $5.2 \times 10^{-8}$ |
| 53 | $4.4 \times 10^{-6}$ | $4.0 \times 10^{-7}$ |
| 54 | $2.9 \times 10^{-7}$ | $8.2 \times 10^{-7}$ |
| 55 | $5.1 \times 10^{-6}$ | $1.0 \times 10^{-7}$ |
| 56 | $4.3 \times 10^{-6}$ | $5.2 \times 10^{-6}$ |
| 57 | $1.3 \times 10^{-6}$ | $3.3 \times 10^{-8}$ |
| 58 | $1.8 \times 10^{-6}$ | $7.5 \times 10^{-7}$ |
| 59 | $1.5 \times 10^{-6}$ | $1.0 \times 10^{-7}$ |
| 60 | $2.0 \times 10^{-6}$ | $5.9 \times 10^{-6}$ |
| 61 | $1.3 \times 10^{-6}$ | $2.5 \times 10^{-8}$ |
| 62 | $3.7 \times 10^{-6}$ | $>1.0 \times 10^{-6}$ |
| 63 | $2.2 \times 10^{-6}$ | $6.0 \times 10^{-8}$ |
| 64 | $1.2 \times 10^{-6}$ | $1.2 \times 10^{-6}$ |
| 65 | $8.6 \times 10^{-7}$ | $1.8 \times 10^{-7}$ |
| 66 | $9.5 \times 10^{-7}$ | $6.0 \times 10^{-6}$ |
| 67 | $3.5 \times 10^{-6}$ | $6.3 \times 10^{-8}$ |
| 68 | $2.7 \times 10^{-6}$ | $8.5 \times 10^{-7}$ |
| 69 | $2.0 \times 10^{-6}$ | $3.5 \times 10^{-8}$ |
| 70 | $2.0 \times 10^{-6}$ | $8.4 \times 10^{-7}$ |
| 71 | $1.7 \times 10^{-6}$ | $7.8 \times 10^{-8}$ |
| 72 | $1.6 \times 10^{-6}$ | $1.0 \times 10^{-6}$ |
| 73 | $2.4 \times 10^{-6}$ | $4.9 \times 10^{-6}$ |
| 74 | $1.9 \times 10^{-6}$ | $1.2 \times 10^{-7}$ |

TABLE 3-continued

Binding Affinity Data for Calcium and Alpha$_1$-adrenoceptors

| Example No. | [$^3$H]-Nitrendipine binding IC$_{50}$ [M] | [$^3$H]-Prazosin binding IC$_{50}$ [M] |
|---|---|---|
| 75 | $8.5 \times 10^{-8}$ | $4.7 \times 10^{-7}$ |
| 76 | $8.5 \times 10^{-8}$ | $1.7 \times 10^{-5}$ |
| 77 | $1.1 \times 10^{-6}$ | $1.1 \times 10^{-7}$ |
| 78 | $1.7 \times 10^{-6}$ | $3.3 \times 10^{-6}$ |

Protocol for Positive Inotropic Effect in Guinea Pig Left Atria

Guinea pigs are killed by cervical dislocation. The left atria are removed and mounted at 1 gm resting tension in tissue baths containing oxygenated Krebs bicarbonate solution which is kept at 37° C. The left atria are electrically paced at 2 Hz with square wave pulses of 1 msec duration. The voltage is set at 1.5×threshold level.

After a one hour equilibration period, control values for developed tension (DT, gm) are recorded. Test compounds are then added to the baths, in a cumulative manner to a maximum concentration of $10^{-4}$, to obtain a concentration-response curve. Treatment values of DT are obtained after the drug effect has reached a plateau and the exposure time for each concentration is 5–8 minutes. Percent change of the treatment value from the control value is calculated at each concentration of the test compound. The results are shown in Table 4 below.

TABLE 4

| Example No. | EC$_{50}$ (M)[a] | Intrinsic Activity[b] |
|---|---|---|
| Control-Bay K8644 | $1.5 \times 10^{-7}$ | 100 |
| 1 | $5.0 \times 10^{-6}$ | 188 |
| 2 | $9.6 \times 10^{-5}$ | 144 |
| 3 | $1.0 \times 10^{-6}$ | 89 |
| 4 | — | 43 |
| 5 | $3.0 \times 10^{-6}$ | 269 |
| 6 | $2.0 \times 10^{-6}$ | 207 |
| 7 | $1.2 \times 10^{-5}$ | 149 |
| 8 | $1.5 \times 10^{-5}$ | 113 |
| 9 | $5.3 \times 10^{-5}$ | 62 |
| 10 | $2.8 \times 10^{-6}$ | 55 |
| 11 | $4.3 \times 10^{-5}$ | 68 |
| 51 | $1.1 \times 10^{-5}$ | 175 |
| 52 | — | 35 |
| 53 | $2.5 \times 10^{-5}$ | 189 |
| 54 | $>1.0 \times 10^{-4}$ | 21 |
| 55 | $1.0 \times 10^{-6}$ | 169 |
| 56 | $4.3 \times 10^{-7}$ | 171 |
| 57 | $2.3 \times 10^{-6}$ | 110 |
| 58 | $8.4 \times 10^{-7}$ | 195 |
| 59 | $2.7 \times 10^{-6}$ | 98 |
| 60 | $1.6 \times 10^{-6}$ | 140 |
| 61 | $1.5 \times 10^{-6}$ | 164 |
| 62 | $>1.0 \times 10^{-4}$ | 48 |
| 63 | $1.2 \times 10^{-5}$ | 75 |
| 64 | $3.4 \times 10^{-6}$ | .76 |
| 65 | $1.0 \times 10^{-6}$ | 225 |
| 66 | $8.5 \times 10^{-7}$ | 210 |
| 67 | $2.4 \times 10^{-5}$ | 86 |
| 68 | $3.7 \times 10^{-6}$ | 147 |
| 69 | $6.2 \times 10^{-5}$ | 60 |
| 70 | $5.0 \times 10^{-6}$ | 132 |
| 71 | — | 40 |
| 72 | $1.2 \times 10^{-5}$ | 70 |
| 73 | $9.8 \times 10^{-7}$ | 84 |

TABLE 4-continued

| Example No. | $EC_{50}$ $(M)^a$ | Intrinsic Activity$^b$ |
|---|---|---|
| 74 | $6.3 \times 10^{-7}$ | 173 |
| 75 | $4.0 \times 10^{-7}$ | 82 |
| 76 | $5.6 \times 10^{-8}$ | 156 |
| 77 | $2.3 \times 10^{-7}$ | 240 |
| 78 | $5.8 \times 10^{-7}$ | 231 |

$^a$$EC_{50}$ (m) = concentration that increases DT by 50% above the control DT.
$^b$Intrinsic Activity is a ratio of the maximum effect of the test compound to that of Bay K8644 and expressed in percent.

The foregoing test results suggest that compounds of this invention have utility in the treatment of congestive heart failure.

Dosage Forms

Compounds of this invention can be administered to treat said deficiencies by any means that produces contact of the active agent with the agent's site of action in the body of the mammal. The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. For use in the treatment of said diseases, a daily dosage of active ingredient can be about 50 to 1000 mg.

Dosage forms (compositions) suitable for administration contain about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions or parenterally, in sterile liquid dosage forms. Alternatively it can be administered sublingually by tablets, gels, pastes, patches or lozenges.

Gelatin capsules contain the active ingredient and powdered carriers, such as lactose, starch, cellulose derivatives, magnesium stearate, stearic acid, and the like. Similar diluents can be used to make compressed tablets. Both tablets can be sugar coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredients, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium benzoate, 1.0 grams of sorbitol solution, U.S.P., and 0.025 milliliters of vanillin.

What is claimed is:

1. A compound of the formula:

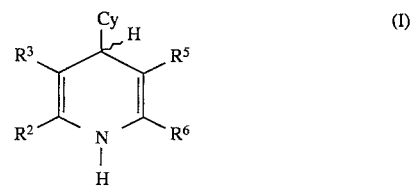

or a pharmaceutically acceptable salt thereof or an optically active isomer or N-oxide thereof wherein:

$R^2$ and $R^6$ independently are alkyl of 1–4 carbon atoms, CN, $CH_2OH$ or $CH_2OCH_2CH_2NH_2$;

$R^3$ independently is $NO_2$, H, CN, or $CONH_2$,

Cy, when R⁵ is CHO, COCH₃, CO₂CH₂CHOHC₆H₅, CO₂CH(OCH₃)C₆H₅, NO₂, CONHC₆H₅ or an alkyl ester of 1–10 carbon atoms, is:

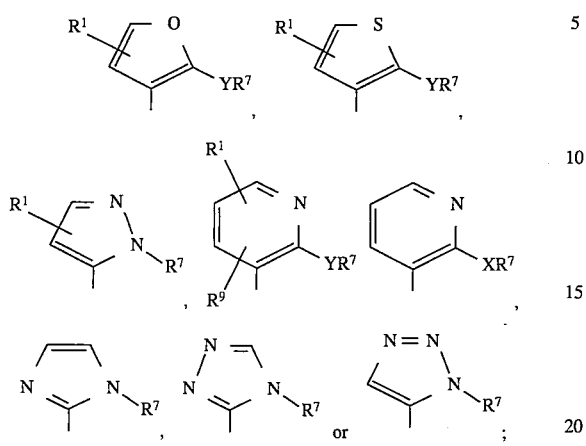

R¹ and R⁹ independently are H, alkyl of 1–4 carbon atoms, haloalkyl of 1–4 carbon atoms, alkoxy of 1–10 carbon atoms, halogen or NO₂;

Cy, when R⁵ is COR⁷, CO₂R⁷ or CONHR⁷, is: 3-, or 4-pyridinyl; 2- or 3-furanyl; 2- or 3-thienyl; 4-, or 5-thiazolyl, 2-, 4-, or 5-pyrimidinyl;

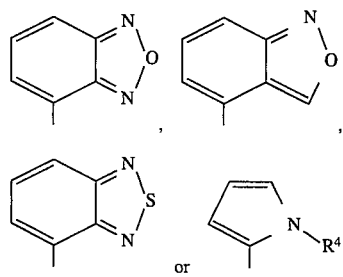

X is SO, SO₂, NR⁴, O, S or N→O;
Y is

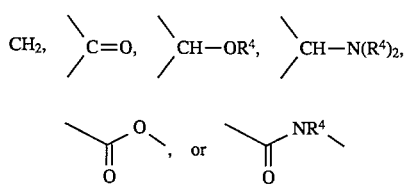

R⁴ is H or an alkyl group of 1–4 carbon atoms;
R⁷ is

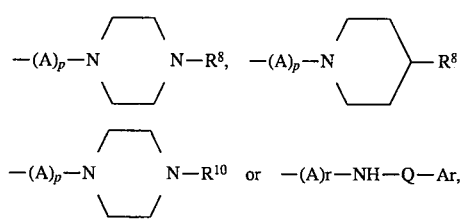

A is a straight or branched alkyl, alkenyl, or alkynyl chain or —(CH₂)ₙCHOHCH₂—;

R¹⁰ is

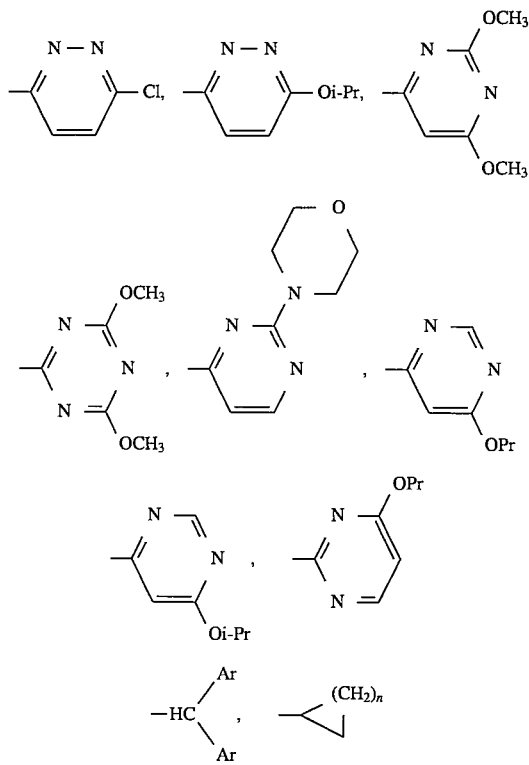

or 2-, 3-, or 4-pyridinyl; 2-, or 4-pyrimidinyl; or 2-pyrazinyl;
R⁸ is

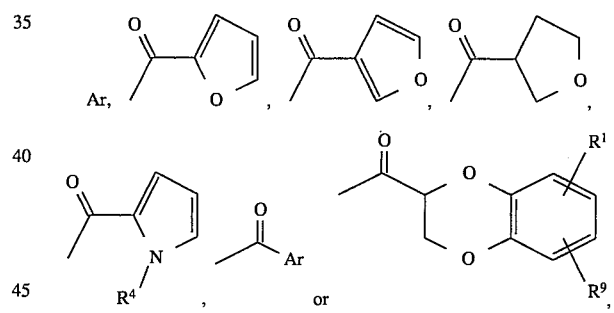

Ar is phenyl optionally substituted with one or two substituents independently selected from the group consisting of: alkyl of 1–4 carbon atoms, haloalkyl of 1–4 carbon atoms, alkoxy of 1–4 carbon atoms, halogen, or NO₂, provided that Ar is not 4-fluorophenyl;

Q is (CH₂)_q, (CH₂)nO, (CH₂)ₙNH or (CH₂)ₙS;
n is independently 1–4;
p is 1 to 10;
q is 0–2; and r is 1 to 10.

2. A compound of claim 1 wherein R² is CH₃.
3. A compound of claim 1 wherein R³ is NO₂.
4. A compound of claim 1 wherein Cy is

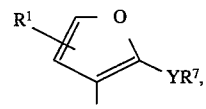

and R⁵ is an alkyl ester of 1–4 carbon atoms.
5. A compound of claim 4 wherein R¹ is H.

6. A compound of claim 4 wherein Y is CH$_2$.
7. A compound of claim 4 wherein R$^7$ is

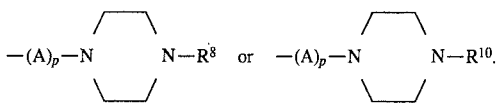

8. A compound of claim 1 wherein:
R$^2$ is CH$_3$;
R$^3$ is NO$_2$;
Cy is

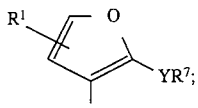

R$^5$ is an alkyl ester of 1–4 carbon atoms;
R$^1$ is H;
Y is CH$_2$; and
R$^7$ is

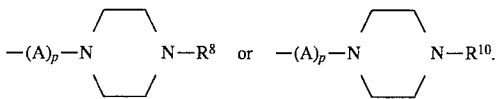

9. A compound of claim 1 wherein Cy is 2- or 3-furanyl, 2- or 3-thienyl, 3-pyridinyl,

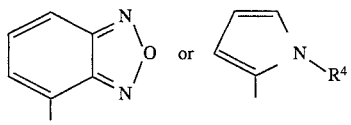

and R$^5$ is CO$_2$R$^7$.

10. A compound of claim 9 wherein R$^7$ is

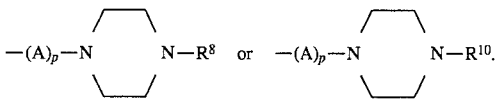

11. A compound of claim 9 wherein R$^4$ is H or an alkyl group of 1–4 carbon atoms.
12. A compound of claim 1 wherein
R$^2$ is CH$_3$;
R$^3$ is NO$_2$;
Cy is 2- or 3-furanyl, 2- or 3-thienyl,

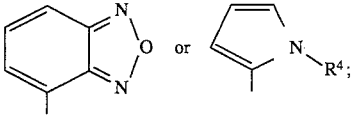

3-pyridinyl,
R$^5$ is CO$_2$R$^7$;

R$^4$ is CH$_3$; and
R$^7$ is

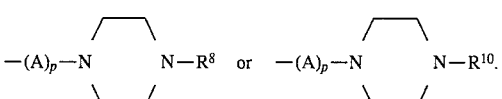

13. The compound of claim 1 which is 4-(4-benzofurazanyl)-1,4-dihydro-2,6-dimethyl-5-nitro-3-pyridinecarboxylic acid, {4-[4-(2-methoxyphenyl)-1-piperazinyl]butyl} ester.
14. The compound of claim 1 which is 1,4-dihydro-2,6-dimethyl-5-nitro-4-(3-pyridinyl)-3-pyridine-carboxylic acid, {4-[4-(2-pyrimidinyl)-1-piperazinyl]-butyl} ester.
15. The compound of claim 1 which is 4-(3-furanyl)-1,4-dihydro-2,6-dimethyl-5-nitro-3-pyridine-carboxylic acid, {2-[4-(2-methoxyphenyl)-1-piperazinyl]-ethyl} ester.
16. The compound of claim 1 which is 4-(3-furanyl)-1,4-dihydro-2,6-dimethyl-5-nitro-3-pyridinecarboxylic acid, {2-[4-(2-pyrimidinyl)-1-piperazinyl]ethyl} ester.
17. The compound of claim 1 which 1,4-dihydro-2,6-dimethyl-4-(1-methyl-1H-pyrrol-2-yl)-5-nitro-3-pyridinecarboxylic acid, {4-[4-(2-methoxyphenyl)1-piperazinyl]-butyl} ester.
18. The compound of claim 1 which is 1,4-dihydro-2,6-dimethyl-4-(1-methyl-1H-pyrrol-2-yl)-5-nitro-3-pyridinecarboxylic acid, {4-[4-(2-pyrimidinyl)-1-piperazinyl]butyl} ester.
19. The compound of claim 1 which is 1,4-dihydro-2,6-dimethyl-5-nitro-4-(3-thienyl)-3-pyridinecarboxylic acid, {2-[4-(2-methoxyphenyl)-1-piperazinyl]ethyl} ester.
20. The compound of claim 1 which is 1,4-dihydro-2,6-dimethyl-5-nitro-4-(3-thienyl)-3-pyridinecarboxylic acid, {2-[4-(2-pyrimidinyl)-1-piperazinyl]ethyl} ester.
21. The compound of claim 1 which is 4-(3-furanyl)-1,4-dihydro-2,6-dimethyl-5-nitro-3-pyridine-carboxylic acid, {4-[4-(2-pyrimidinyl)-1-piperazinyl]-butyl} ester.
22. The compound of claim 1 which is 4-(2-furanyl)-1,4-dihydro-2,6-dimethyl-5-nitro-3-pyridinecarboxylic acid, {4-[4-(2-pyrimidinyl)-1-piperazinyl]butyl} ester.
23. The compound of claim 1 which is 1,4-dihydro-2,6-dimethyl-5-nitro-4-(2-thienyl)-3-pyridinecarboxylic acid, {2-[4-(2-methoxyphenyl)-1-piperazinyl]ethyl} ester.
24. The compound of claim 1 which is 1,4-dihydro-2,6-dimethyl-4-(1-methyl-1H-pyrrol-2-yl)-5-nitro-3-pyridinecarboxylic acid, {2-[4-(2-methoxyphenyl)-1-piperazinyl]ethyl} ester.
25. The compound of claim 1 which is 1,4-dihydro-2,6-dimethyl-4-(1-methyl-1H-pyrrol-2-yl)-5-nitro-3-pyridinecarboxylic acid, {2-[4-(2-pyrimidinyl)-1-piperazinyl]ethyl} ester.
26. A pharmaceutical composition comprising a pharmaceutically acceptable carrier and a therapeutically effective amount of a compound of claim 1.
27. A method for treating congestive heart failure in a mammal which comprises administering to the mammal a therapeutically effective amount of a compound of claim 1.

* * * * *